(12) United States Patent
Baikie

(10) Patent No.: US 8,866,505 B2
(45) Date of Patent: Oct. 21, 2014

(54) MEASUREMENT APPARATUS

(71) Applicant: KP Technology Ltd., Wick (GB)

(72) Inventor: Iain Baikie, Wick (GB)

(73) Assignee: KP Technology Ltd. (GB)

( * ) Notice: Subject to any disclaimer, the term of this patent is extended or adjusted under 35 U.S.C. 154(b) by 0 days.

(21) Appl. No.: 14/117,851

(22) PCT Filed: Feb. 21, 2013

(86) PCT No.: PCT/GB2013/050427
§ 371 (c)(1),
(2), (4) Date: Nov. 14, 2013

(87) PCT Pub. No.: WO2013/124663
PCT Pub. Date: Aug. 29, 2013

(65) Prior Publication Data
US 2014/0084902 A1 Mar. 27, 2014

(30) Foreign Application Priority Data
Feb. 24, 2012 (GB) .................................. 1203186.0

(51) Int. Cl.
*G01R 31/20* (2006.01)
*G01N 27/00* (2006.01)
*G01Q 60/30* (2010.01)
*B82Y 35/00* (2011.01)

(52) U.S. Cl.
CPC ............... *G01N 27/002* (2013.01); *B82Y 35/00* (2013.01); *G01Q 60/30* (2013.01)
USPC ................................. 324/754.01; 324/750.14

(58) Field of Classification Search
CPC . G01N 27/002; G01N 23/2251; G01Q 60/30; G01Q 60/40; G01R 1/071; G02F 1/293; Y10S 977/783; Y10S 977/784; Y10S 977/788
See application file for complete search history.

(56) References Cited

U.S. PATENT DOCUMENTS

| 4,823,368 | A | 4/1989 | Uda et al. |
| 7,116,115 | B2 * | 10/2006 | Gianchandani et al. ...... 324/661 |
| 2003/0175945 | A1 | 9/2003 | Thompson et al. |
| 2006/0256332 | A1* | 11/2006 | Sandstrom .................... 356/317 |

FOREIGN PATENT DOCUMENTS

| GB | 2439439 A | 12/2007 |
| GB | 2439439 A9 * | 12/2007 |
| GB | 2443280 A | 4/2008 |
| JP | 9162253 A | 12/1995 |

(Continued)

OTHER PUBLICATIONS

"Low cost PC based scanning Kelvin probe," by I. D. Baikie and P. J. Estrup, published in Review of Scientific Instruments, vol. 69, No. 11, Nov. 1998.

(Continued)

*Primary Examiner* — Vinh Nguyen
(74) *Attorney, Agent, or Firm* — One3 IP Management, P.C.; Jeromye V. Sartain

(57) ABSTRACT

A measurement apparatus for surface analysis carried out in a gaseous environment such as air comprises a measurement device capable of measuring a contact potential difference between a probe and a surface, and a light source that triggers photoelectric emission from a sample. The apparatus may operate in "dual" photoemission and contact potential difference (CPD) measurement modes.

26 Claims, 32 Drawing Sheets

(56) References Cited

FOREIGN PATENT DOCUMENTS

| JP | 11094780 | A | 9/1997 |
|---|---|---|---|
| JP | 3481031 | B2 | 12/2003 |
| WO | 0190730 | A2 | 11/2001 |
| WO | 2005001459 | A2 | 1/2005 |

OTHER PUBLICATIONS

"Direct comparison of photoemission spectroscopy and in situ Kelvin probe work function measurements on indium tin oxide films," by M.M. Beerborn, et al., published in the Journal of Electron Spectroscopy, 2006.

"Kelvin probe and ultraviolet photoemission measurements of indium tin oxide work function: a comparison," by J.S. Kim et al., published in Synthetic Metals, 2000.

"Surface States and Photovoltaic Effects in CdSe Quantum Dot Films," by L. Kronik et al, published in Journal of Electrochemical Society, vol. 145, No. 5, May 1998.

"A Novel Approach for True Work Function Determination of Electron-Emissive Materials by Combined Kelvin Probe and Photoelectric Measurements," by Bert Lagel et al., published in Mat. Res. Soc. Symp. Proc., vol. 621, 2000.

"Photoelectron Spectroscopy" product specification for "Model AC-2," published by RKI Instruments, Inc.

"Photoelectron Spectrophotometer in Air Surface Analyzer" product specification for "Model AC-3," published by RKI Instruments, Inc.

\* cited by examiner

MEASUREMENT APPARATUS

The present disclosure relates to a measurement apparatus, and in particular to apparatus and related methods for measuring work function properties of a sample surface.

Measurement devices capable of measuring a contact potential difference between a probe and a surface are known. An example is the Kelvin probe, which is a non-contact, non-destructive measurement device used to investigate properties of materials. The Kelvin probe is generally used for measuring the work function difference between a specimen and a reference material (typically a vibrating tip). The work function is a sensitive indicator of surface condition and is affected by adsorbed or evaporated layers, surface construction, surface charging, oxide layer imperfections and surface and bulk contamination, as well as many other factors. The work function is a material property that can be defined as the minimum amount of energy that must be applied to a surface of a material in order to remove an electron from the material so that it can just exist outside the boundary of the material in vacuum conditions.

A technique for measuring work function of a surface involves bringing two conducting materials into electrical contact and quantifying the flow of charge from one material to the other. One of the conducting materials is typically a reference material having a documented value for work function and the other conducting material has a value of work function which is required to be measured relative to the reference.

When two conducting materials with different values of work function are electrically connected to one another, electrons in the material with the lower work function flow to the material with the higher work function. If the conducting materials are assembled to form the plates of a parallel plate capacitor, equal and opposite surface charges form on the plates.

The potential difference developed between the plates of the capacitor is called the contact potential and it may be measured by applying an external backing potential to the capacitor until the surface charges on the plates disappear. At this point, commonly referred to as the null output, the backing potential is equal to the contact potential difference (CPD). This can be referred to as a "null based" technique for measuring CPD. CPD can be defined as the measured change in the contact potential between the reference material and the specimen surface.

It is also known to make use of the photoelectric effect to analyse surfaces. This effect is the basis for techniques including photoemission spectroscopy, also known as photoelectron spectroscopy. Techniques relying on photoelectric emission of electrons will be referred to herein as "PE" (photo emission) techniques. According to this technique light, typically from an ultra-violet (UV) source is incident on a (conducting) material, such as a metal or semiconductor. The incident particles of light (photons) have sufficient energy to allow electrons near the surface of the material to escape. The energy required for electrons to escape the material is termed the (photoelectric) work function. The emitted electrons can be detected and resolved by energy or angle to determine characteristics of the material.

If the ejected electrons can be detected, for instance by a metallic electrode located near the surface of the material, then the work function of the material can be determined by varying the energy of the incoming photons. Photons having insufficient energy will not liberate electrons, while photons of just sufficient energy will liberate a few electrons and photons of much more energy than the work function will liberate a lot of electrons. This technique is termed an absolute technique, in that it directly produces a value for work function. Current PE instruments can typically resolve to about 0.050-0.100 eV resolution, with a measurement duration of 5-10 minutes.

According to a first aspect of the disclosure there is provided a measurement apparatus comprising: a measurement device capable of measuring a contact potential difference between a probe and a surface; and a light source; wherein the light source is configured to, in use, emit radiation for triggering photoelectric emission from a sample which is provided on or forms the surface; characterised in that the probe and the surface are exposed to or housed within a gaseous environment.

Optionally the gaseous environment comprises air.

Optionally, the apparatus further comprises a housing containing the probe and/or the surface, and the environment within said housing is controlled to provide a gaseous environment having gas or air with a controlled relative humidity or a controlled gas such as nitrogen.

Optionally, the measurement device comprises a Kelvin probe.

Optionally the apparatus further comprises means to vary the potential applied to the probe through a voltage range.

Optionally radiation emitted from the light source is of constant intensity (DC).

Optionally radiation emitted from the light source is modulated (AC).

Optionally the apparatus comprises an optical chopper.

Optionally, peak to peak current data is obtained in a selective window averaging fashion.

Optionally, phase information can be used to reduce the effective noise.

Optionally, the CPD voltage is determined by an off null linear extrapolation technique.

Optionally, the probe is selectively operable in a first mode wherein the probe and the surface oscillate with respect to each other with a component of motion in a direction normal to the surface for the performance of a relative work function measurement and a second mode wherein, for successive measurements, the probe is in a fixed relation to the surface in a direction normal to the surface for the performance of an absolute work function measurement derived from detected photoelectric emission.

According to a second aspect of the disclosure there is provided a measurement apparatus comprising: a measurement device capable of measuring a contact potential difference between a probe and a surface; and a light source; wherein the light source is configured to, in use, emit radiation for triggering photoelectric emission from a sample which is provided on or forms the surface; characterized in that the probe is selectively operable in a first mode wherein the probe and the surface oscillate with respect to each other with a component of motion in a direction normal to the surface for the performance of a relative work function measurement and a second mode wherein, for successive measurements, the probe is in a fixed relation to the surface in a direction normal to the surface for the performance of an absolute work function measurement derived from detected photoelectric emission.

Optionally, the apparatus is arranged to perform measurements in the first and second modes simultaneously or quasi-simultaneously.

The term "quasi-simultaneously" refers to generating signals for one mode of operation with a first frequency and generating signals for another mode of operation with a second, different, frequency. This can for example be achieved by chopping the light at a first frequency for the photoelectric emission based absolute work function measurement, while vibrating the tip at a different frequency for the contact potential difference based relative work function measurement. Multiple modes can be encoded in this quasi-simultaneous fashion by using successively higher frequencies.

Optionally the light source is an ultra-violet broad band source.

Optionally the light source comprises one or more light emitting diodes.

Optionally, multiple LEDs can be individually automatically or selectively controlled in respect of one or more of their intensity, phase and modulation frequency characteristics.

Optionally the apparatus comprises a wavelength selector through which the radiation emitting from the light source is filtered.

Optionally, the apparatus comprises a light source emitting radiation in the visible and/or infra-red ranges.

Optionally, the light source is arranged to emit a single frequency of light for the performance of a surface photo-voltage technique. Alternatively, a broadband source could be used. In that case the broadband source can be employed without any form of filtering.

Optionally, the frequency of light emitted from the light source may be varied to perform a surface photo-voltage spectroscopy method. Alternatively, a broadband source could be used. In that case the broadband source can be employed without any form of filtering. Optionally the apparatus comprises a mechanism for scanning the sample with respect to a probe tip to map out the parameters across the surface of the sample.

Optionally, the apparatus comprises a UV source with a chopper and a visible/infra-red source with a chopper; and a chopping frequency of the UV light source can be selected to be different to a chopping frequency of the visible/infra-red light source so that measurements using the two different light sources can be conducted in a simultaneous or quasi-simultaneous fashion.

Optionally, the apparatus can be used with a sample that comprises a (bulk) metal, metal alloy, semiconductor, insulator, liquid, polymer, composite, conducting polymer, biological tissue, powder or liquid surface with or without a thin film.

Optionally, a tip of the probe has a circular geometry and comprises a section or sections removed to enhance by reflection the amount of light incident on the sample surface.

Optionally, the apparatus is arranged for the performance of a surface density of states (DOS) spectroscopic method, wherein a probe tip is held at a constant positive voltage and is held in fixed relation to the surface; the energy of photons is scanned, the photoemission current is detected in either DC or AC mode; and DOS information is obtained by differentiating the integral current.

Optionally, the apparatus is arranged for the performance of a surface density of states (DOS) spectroscopic method, wherein the Photon energy is held constant at an energy resulting in photoemission, a probe tip is held in fixed relation to the surface; the tip potential is scanned through a voltage range; the photoemission current is detected in either DC or AC mode; and DOS information is obtained by differentiating the integral current.

According to a third aspect of the disclosure there is provided a method of analysing a surface comprising the steps of measuring a contact potential difference between a probe and a surface; and emitting radiation for triggering photoelectric emission from a sample which is provided on or forms the surface; characterised in that the probe and the surface are exposed to or housed within a gaseous environment.

It will also be understood that the disclosure also includes methods corresponding to the various arrangements and capabilities of the apparatus and the uses thereof. These methods can be derived from the characteristics of the apparatus mentioned above, and from the description which follows together with the accompanying figures.

According to a fourth aspect of the disclosure there is provided a method of analysing a surface comprising the steps of measuring a contact potential difference between a probe and a surface; emitting radiation to trigger photoelectric emission from a sample which is provided on or forms the surface; and selectively operating the apparatus in a first mode wherein the probe and the surface oscillate with respect to each other with a component of motion in a direction normal to the surface for the performance of a relative work function measurement or a second mode wherein, for successive measurements, the probe is in a fixed relation to the surface in a direction normal to the surface for the performance of an absolute work function measurement derived from detected photoelectric emission.

According to a fifth aspect of the disclosure there is provided a computer program product encoded with instructions that when run on a computer, cause the computer to act as a control mechanism for the apparatus and the methods mentioned above.

The computer program product may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fibre optic cable, twisted pair, digital subscriber line (DSL), or wireless technologies such as infra-red, radio, and microwave, then the coaxial cable, fibre optic cable, twisted pair, DSL, or wireless technologies such as infra-red, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

The present invention will now be described, by way of example only, with reference to the accompanying drawings, in which.

Figure 10:
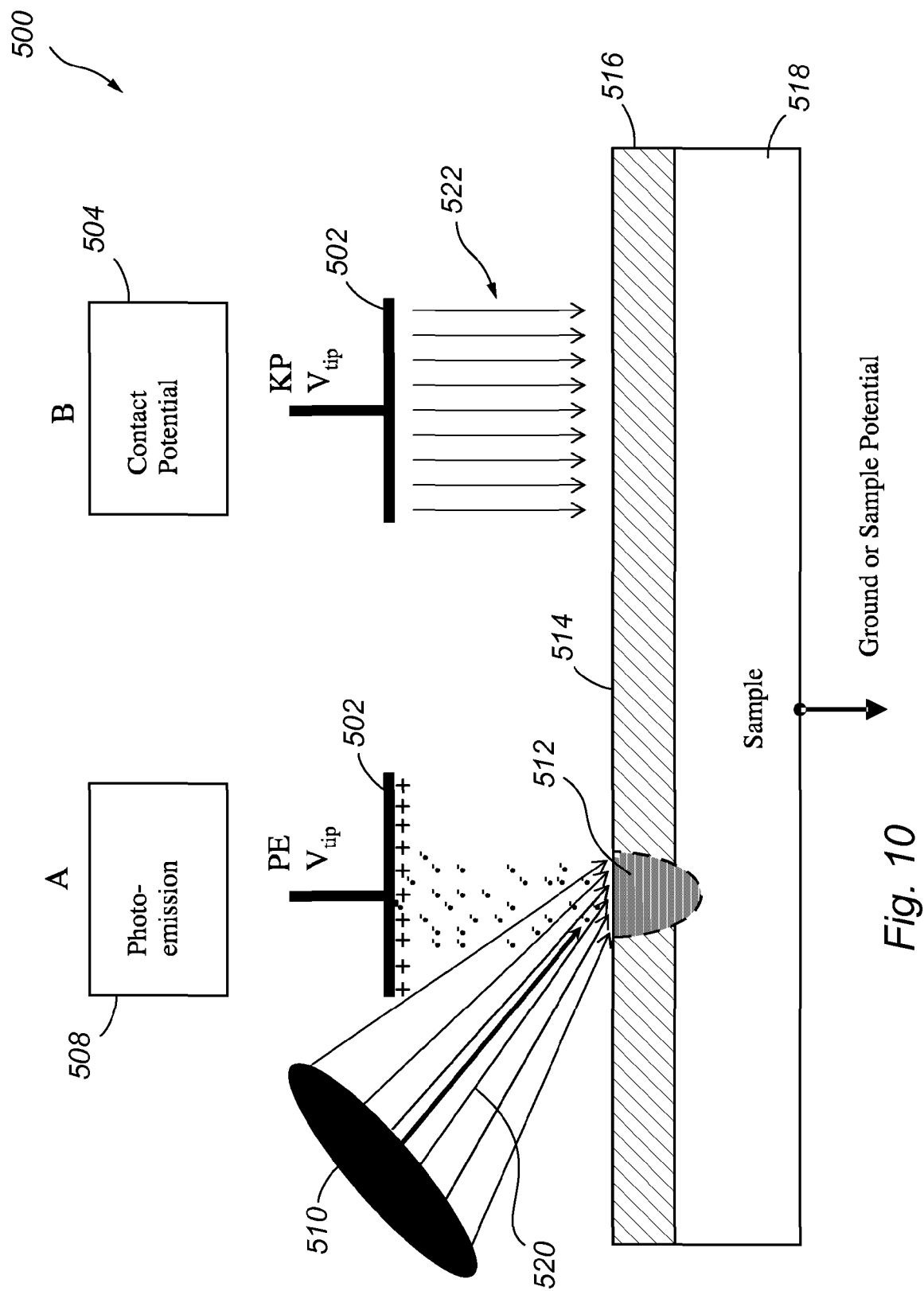
FIG. 10 shows a dual mode detection system, comprising a tip for operation in a photoemission measurement mode and a contact potential measurement apparatus.
Figure 11:
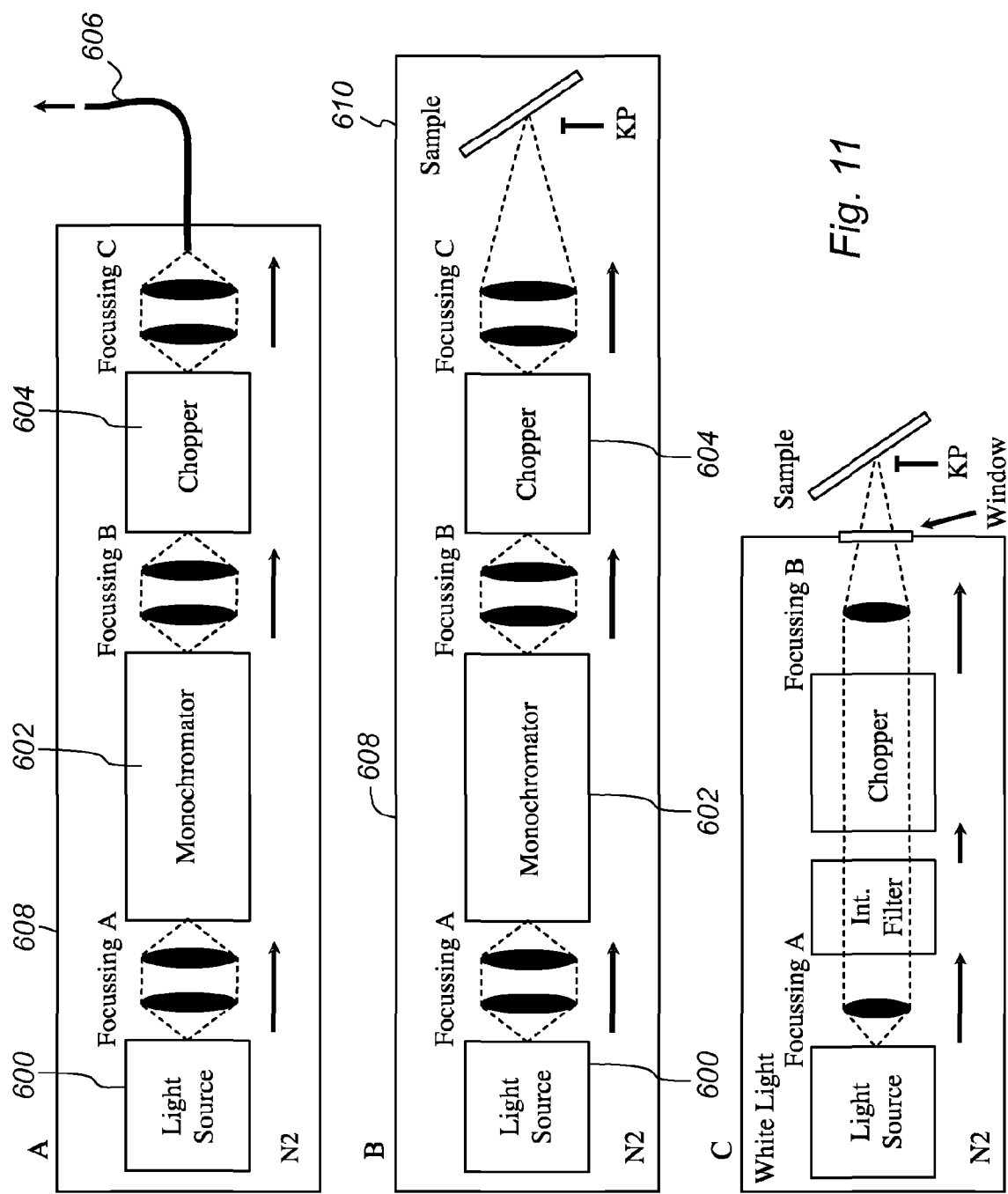
Figure 12:
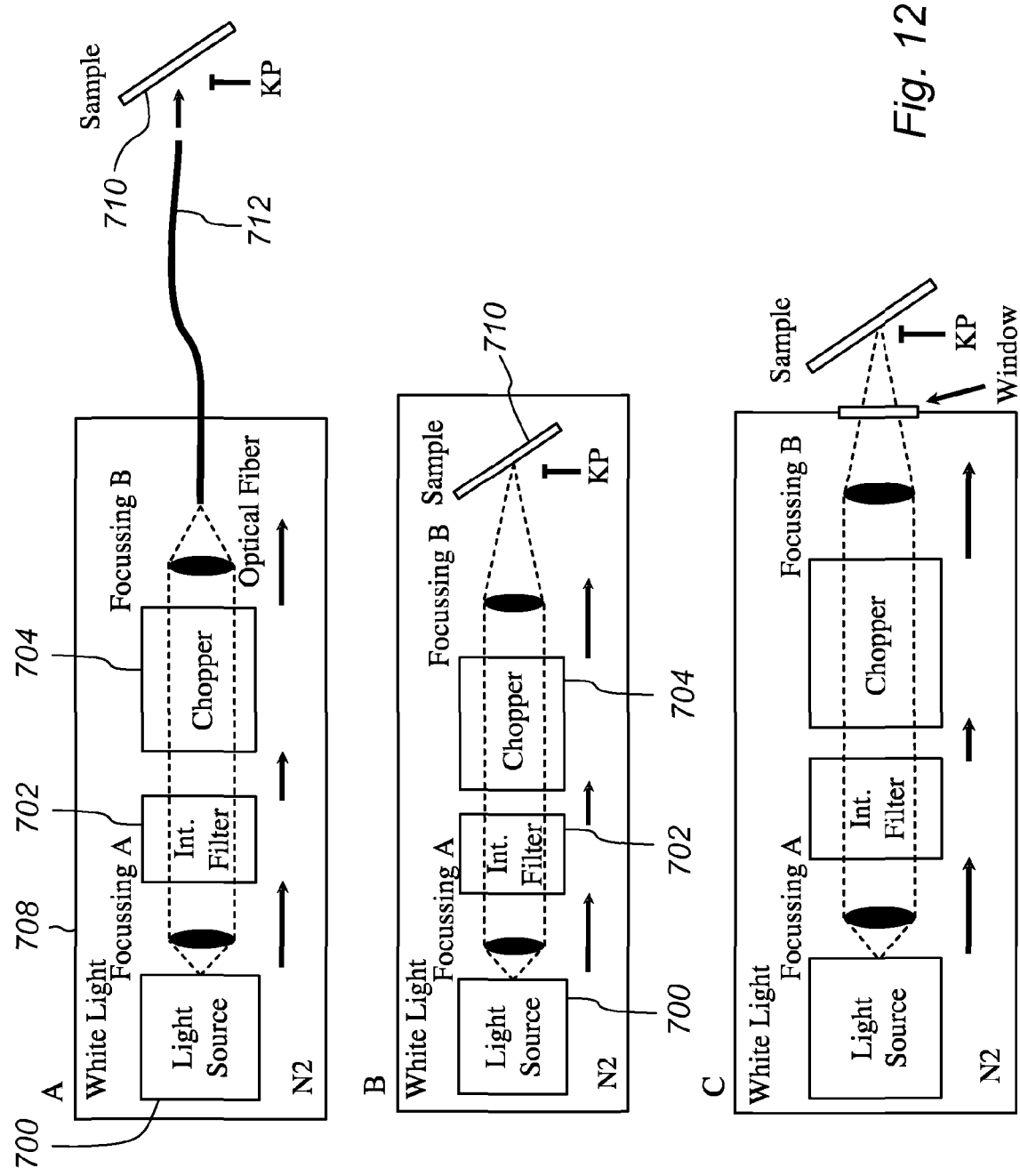
Figure 13:
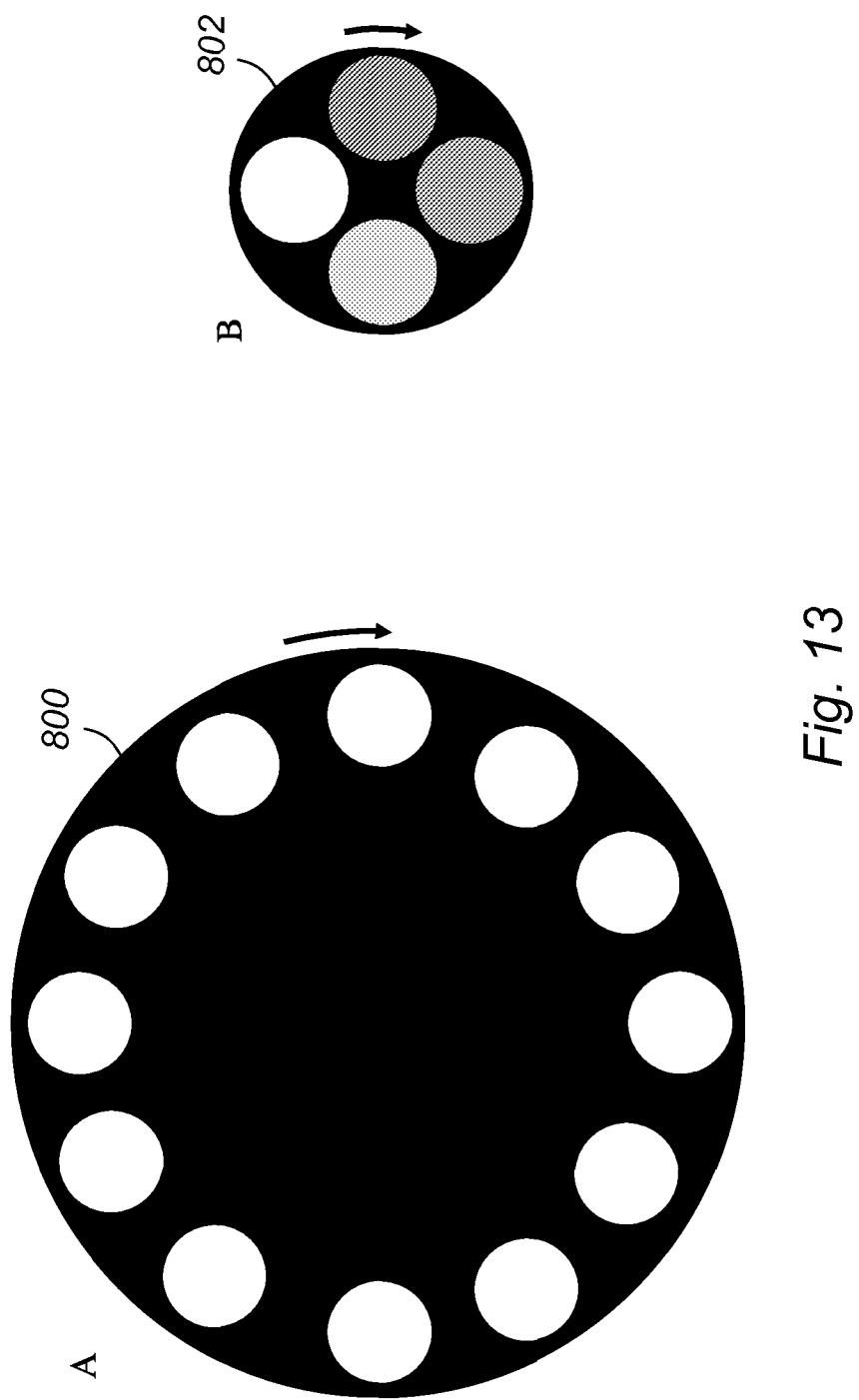
Figure 14:
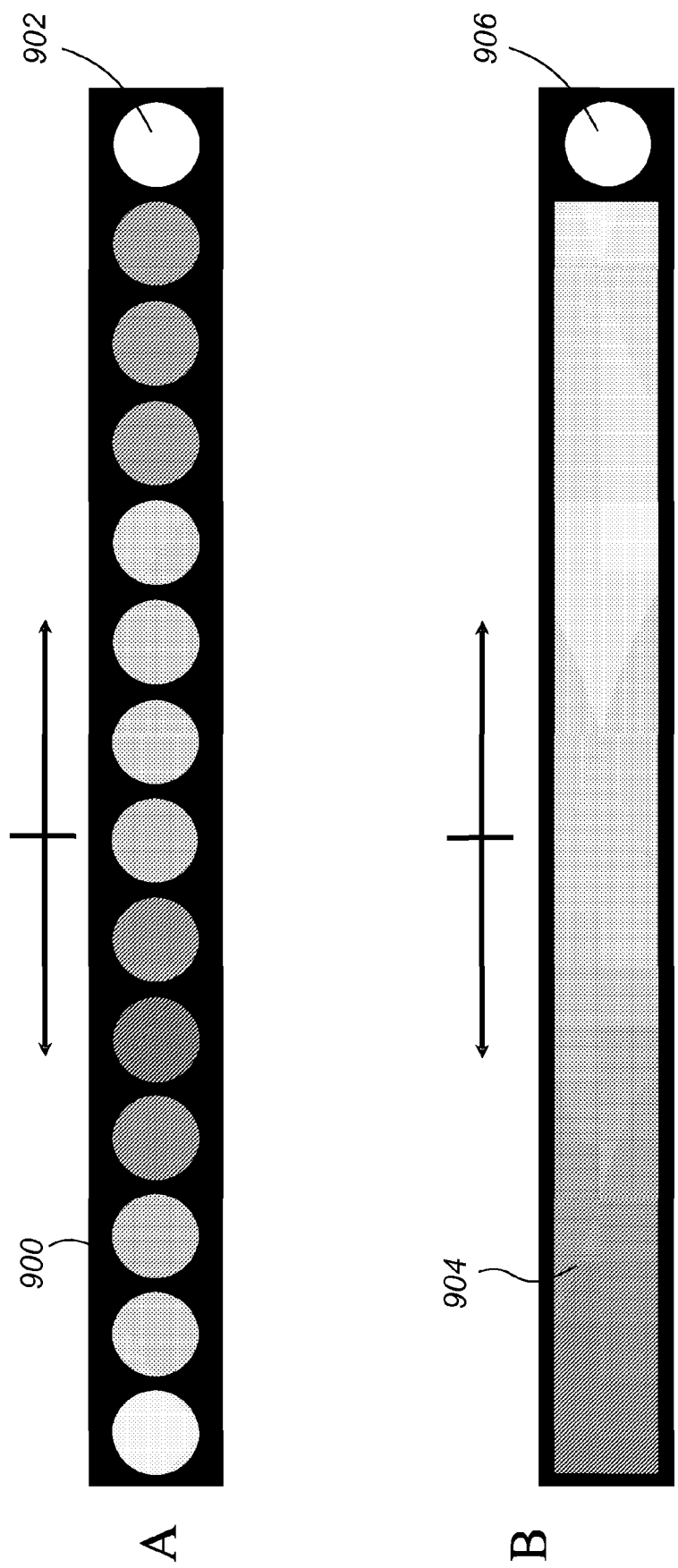
Figure 15:
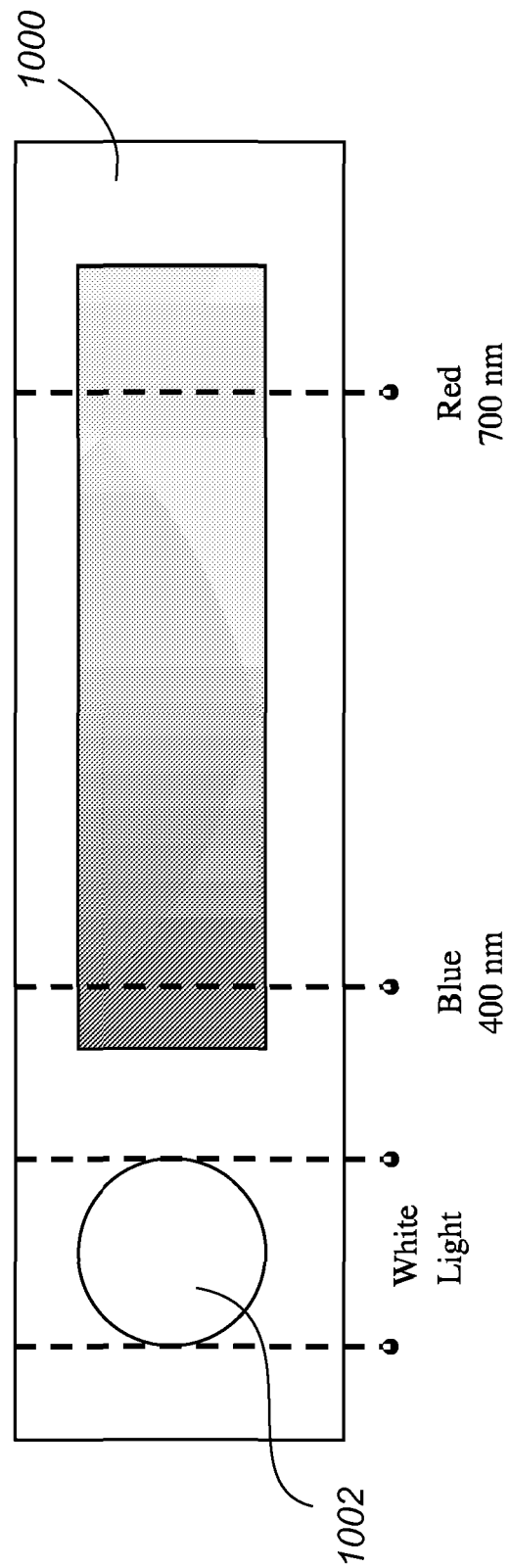
Figure 16:
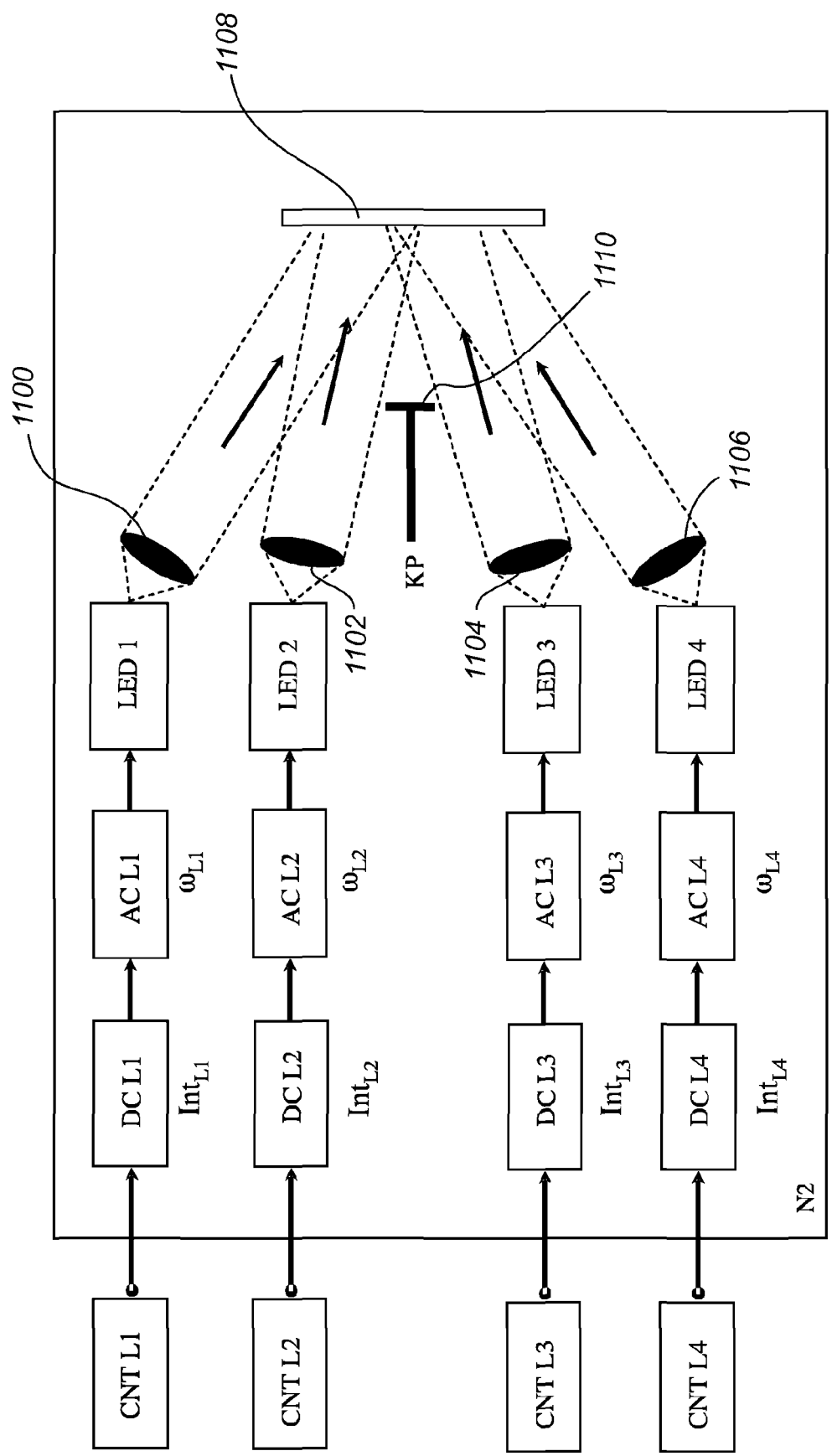
Figure 17:
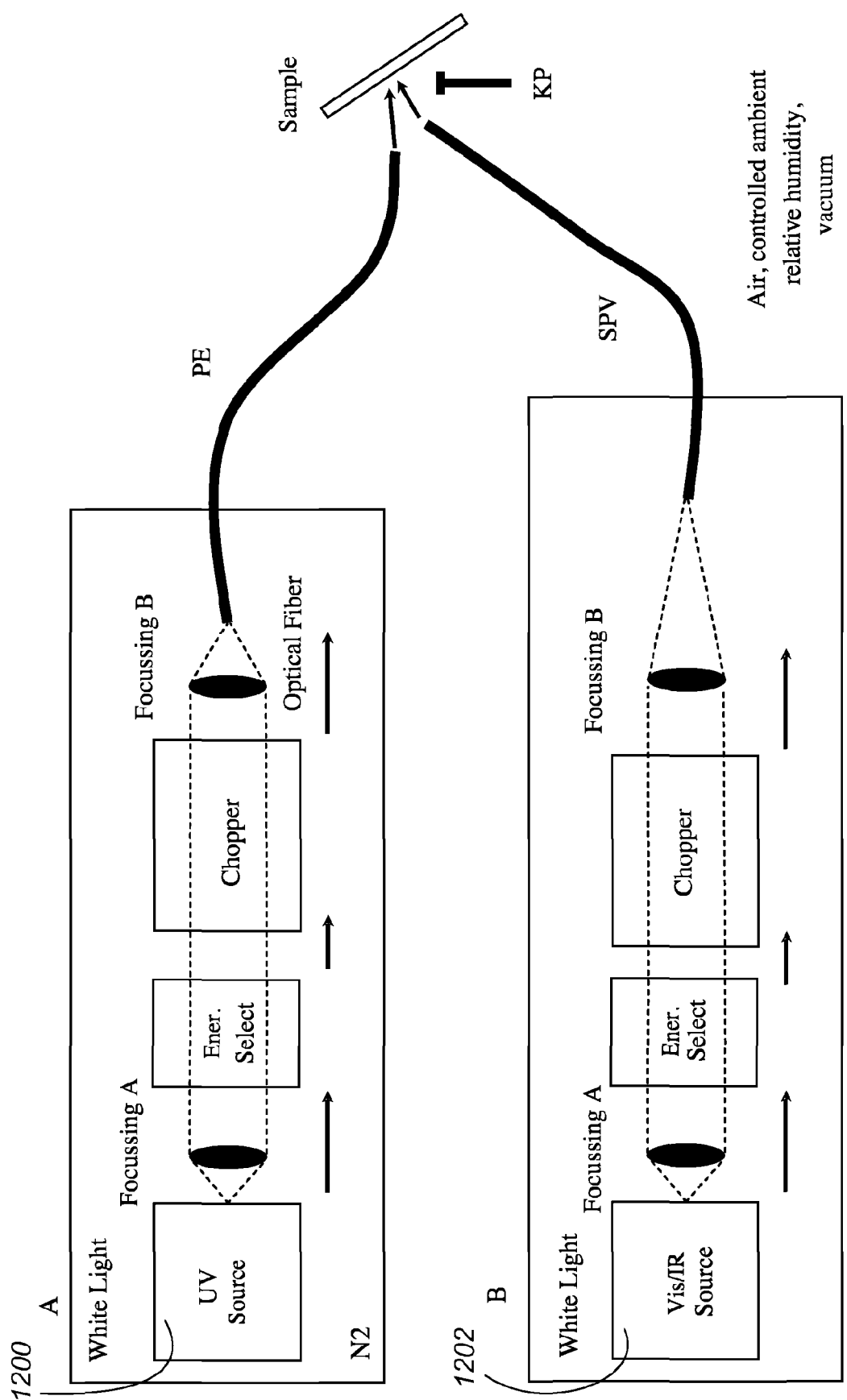
Figure 18:
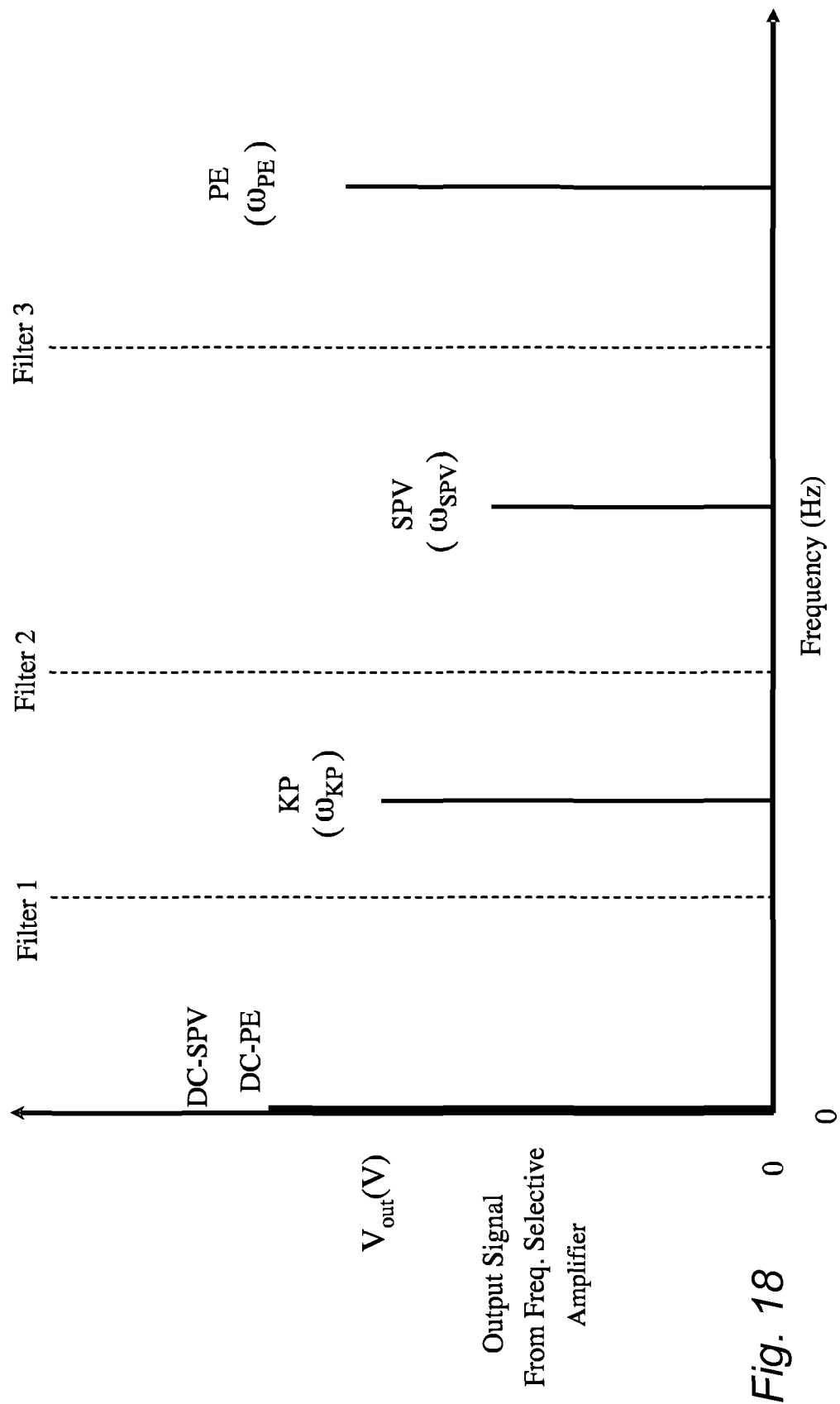
Figure 19:
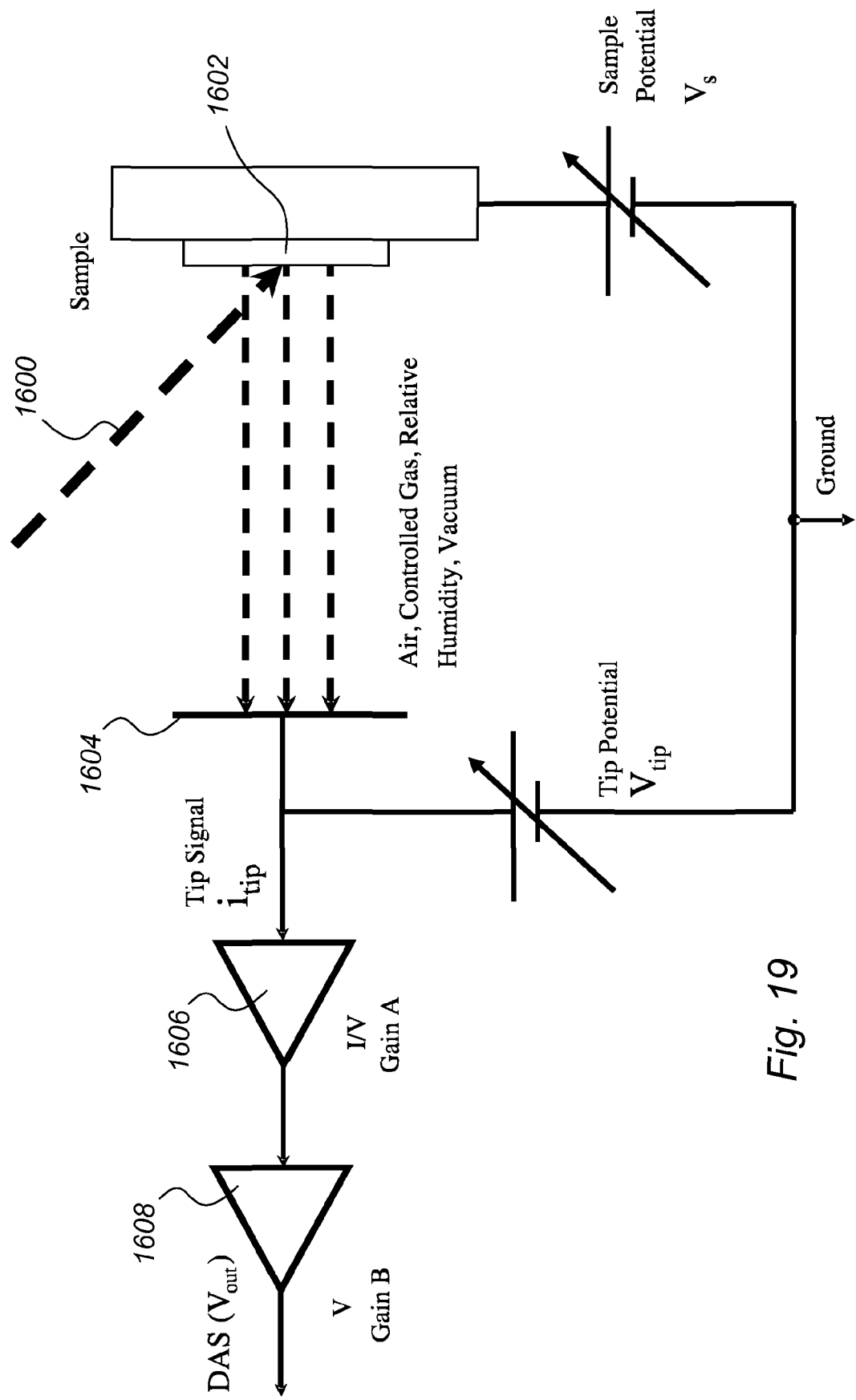
Figure 20:
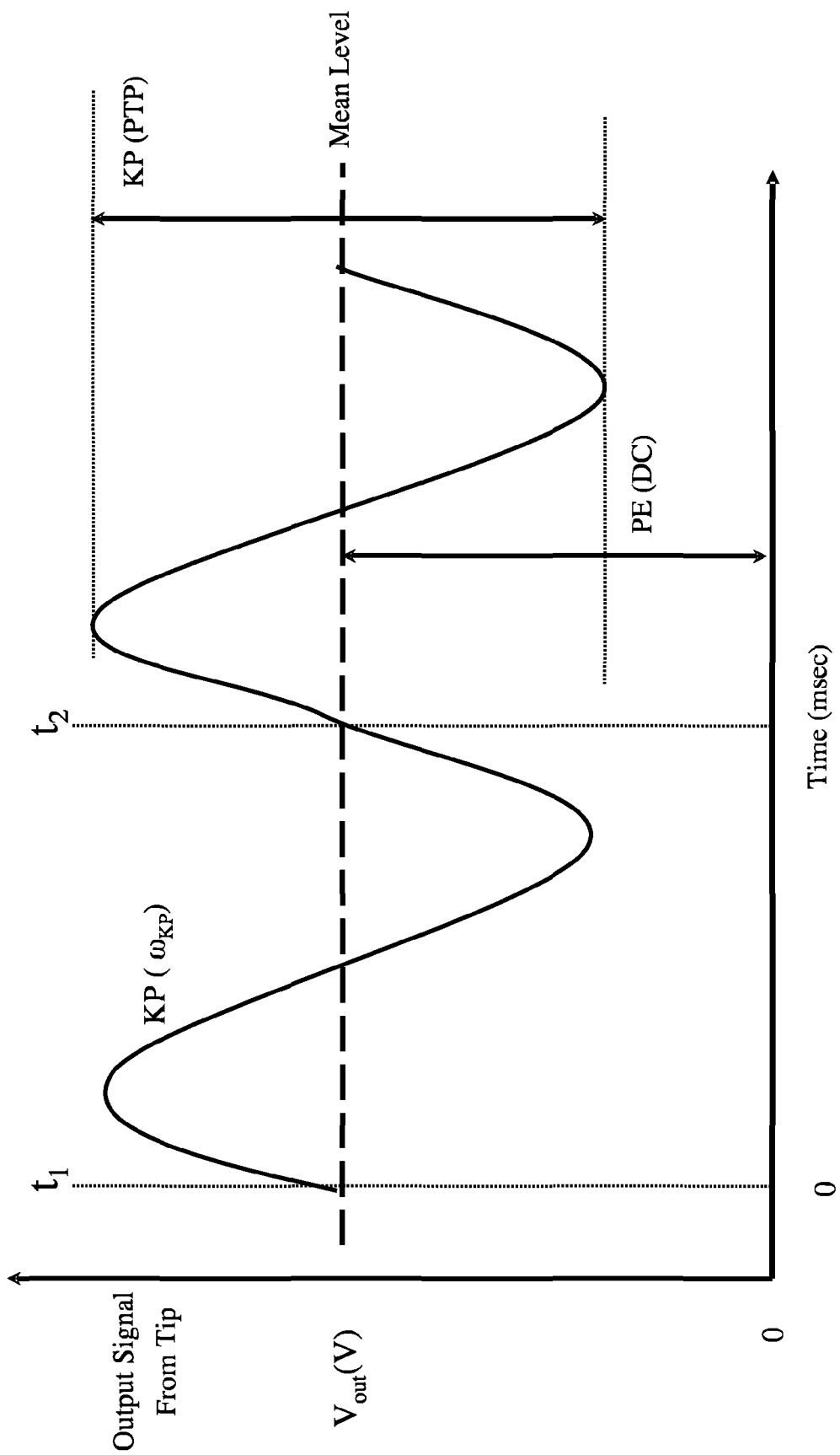
Figure 21:
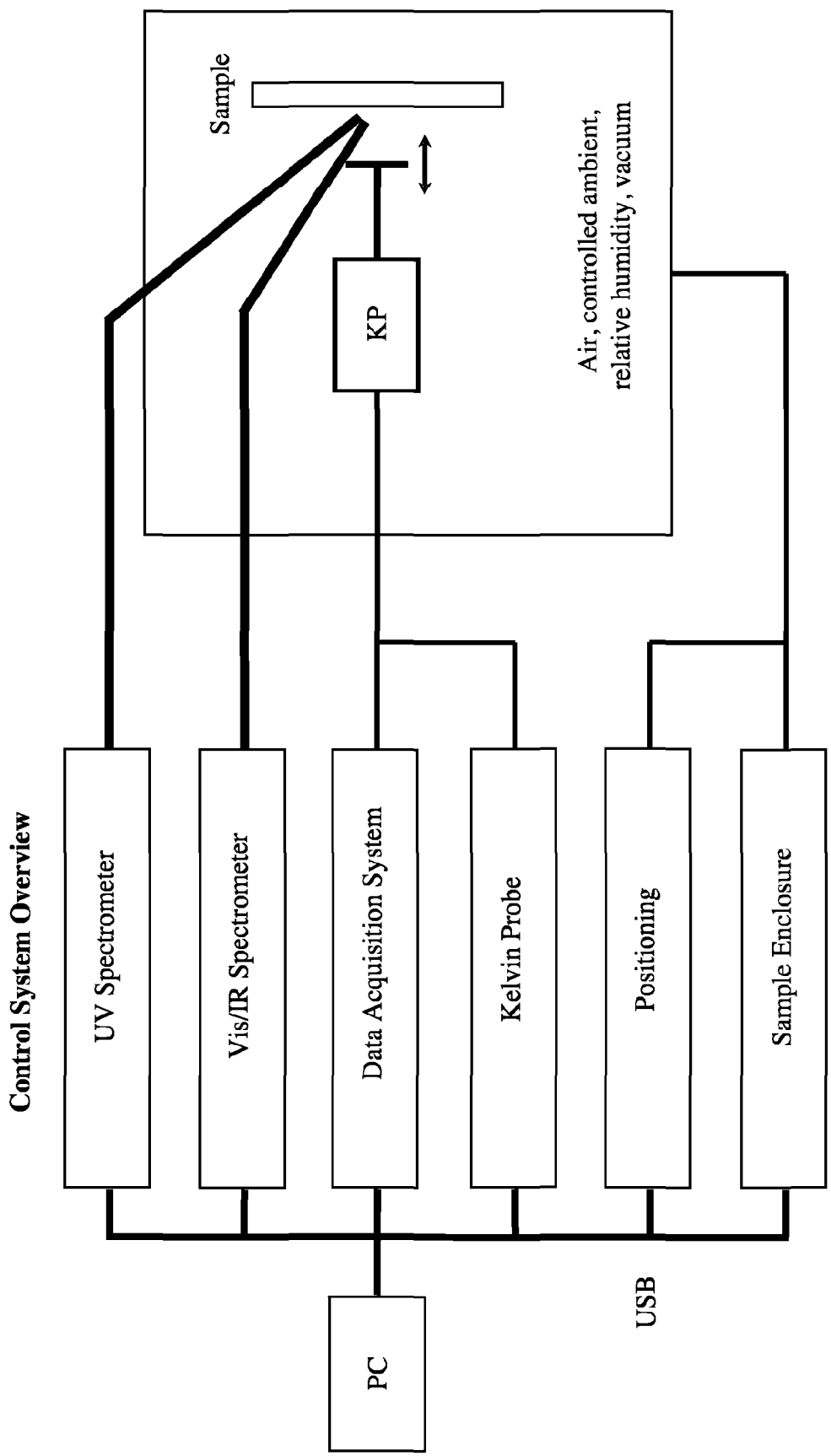
Figure 22:
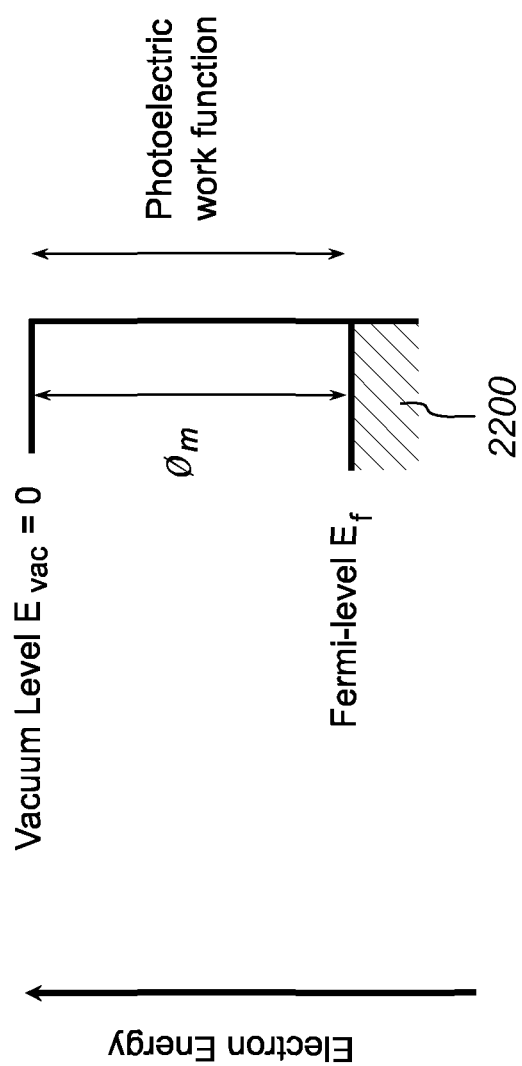
Figure 23:
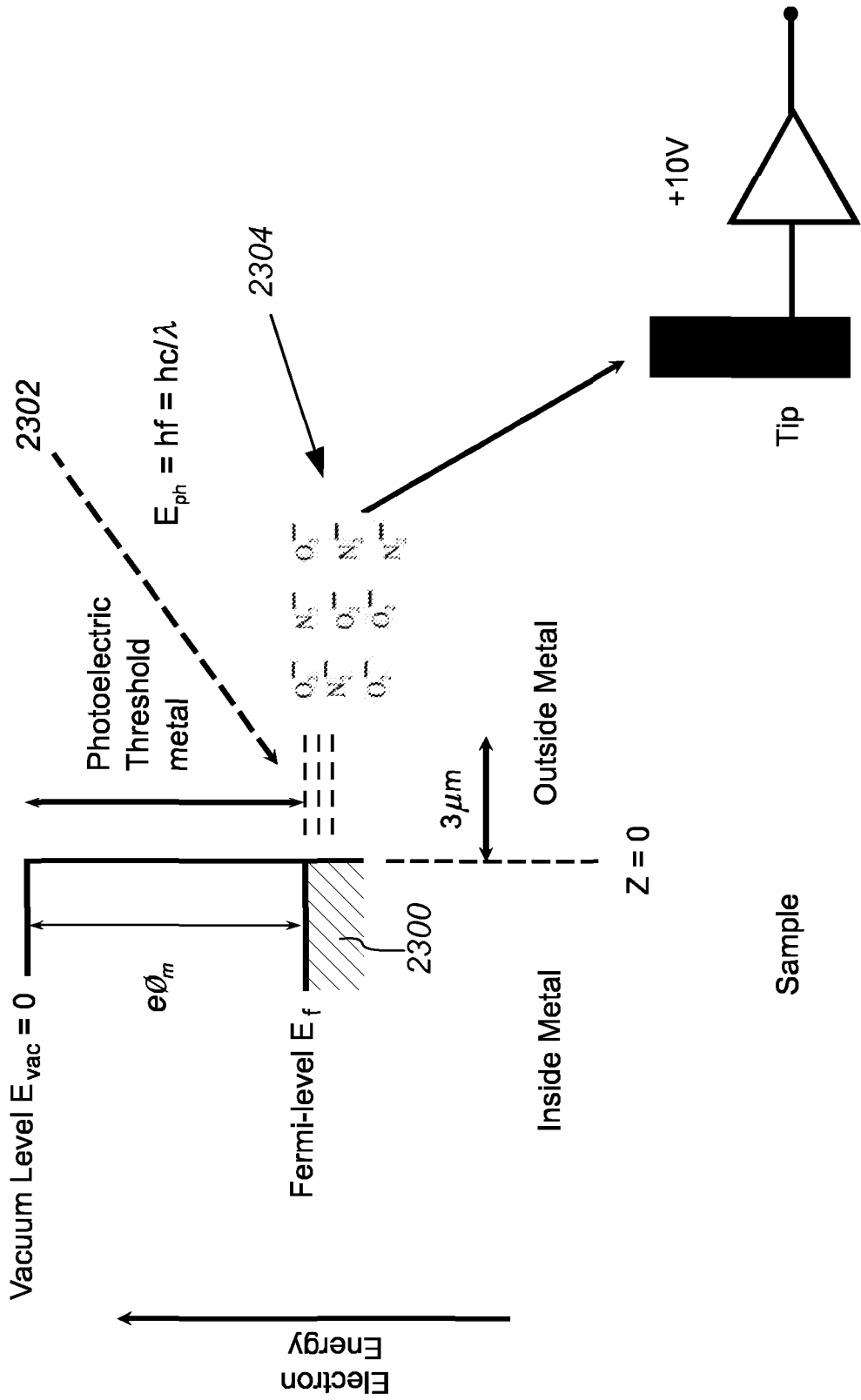
Figure 24:
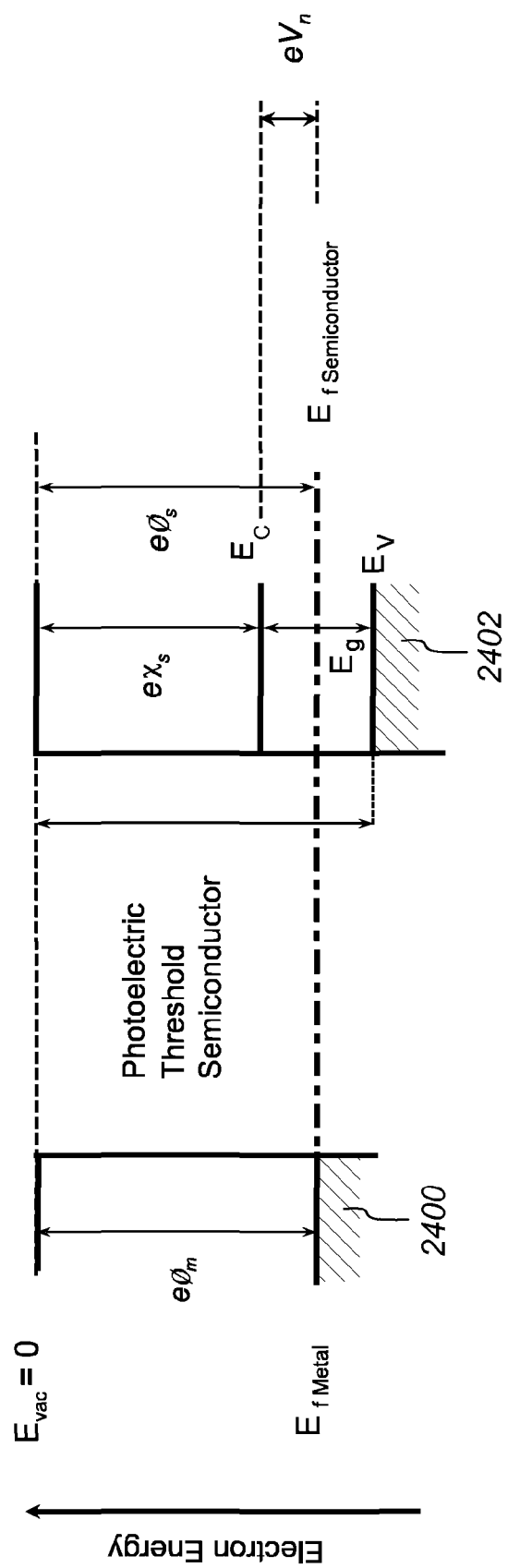
Figure 25:
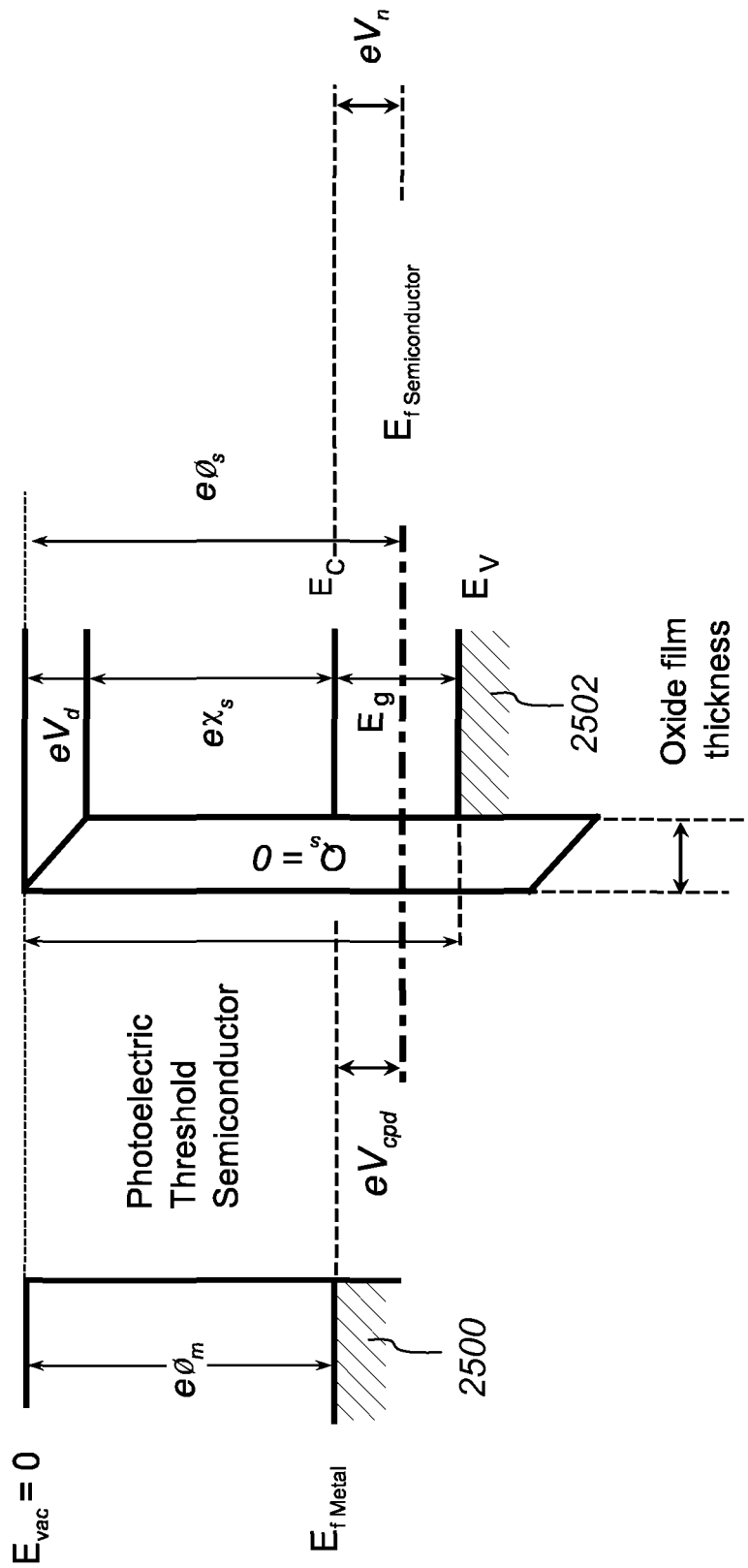
Figure 26:
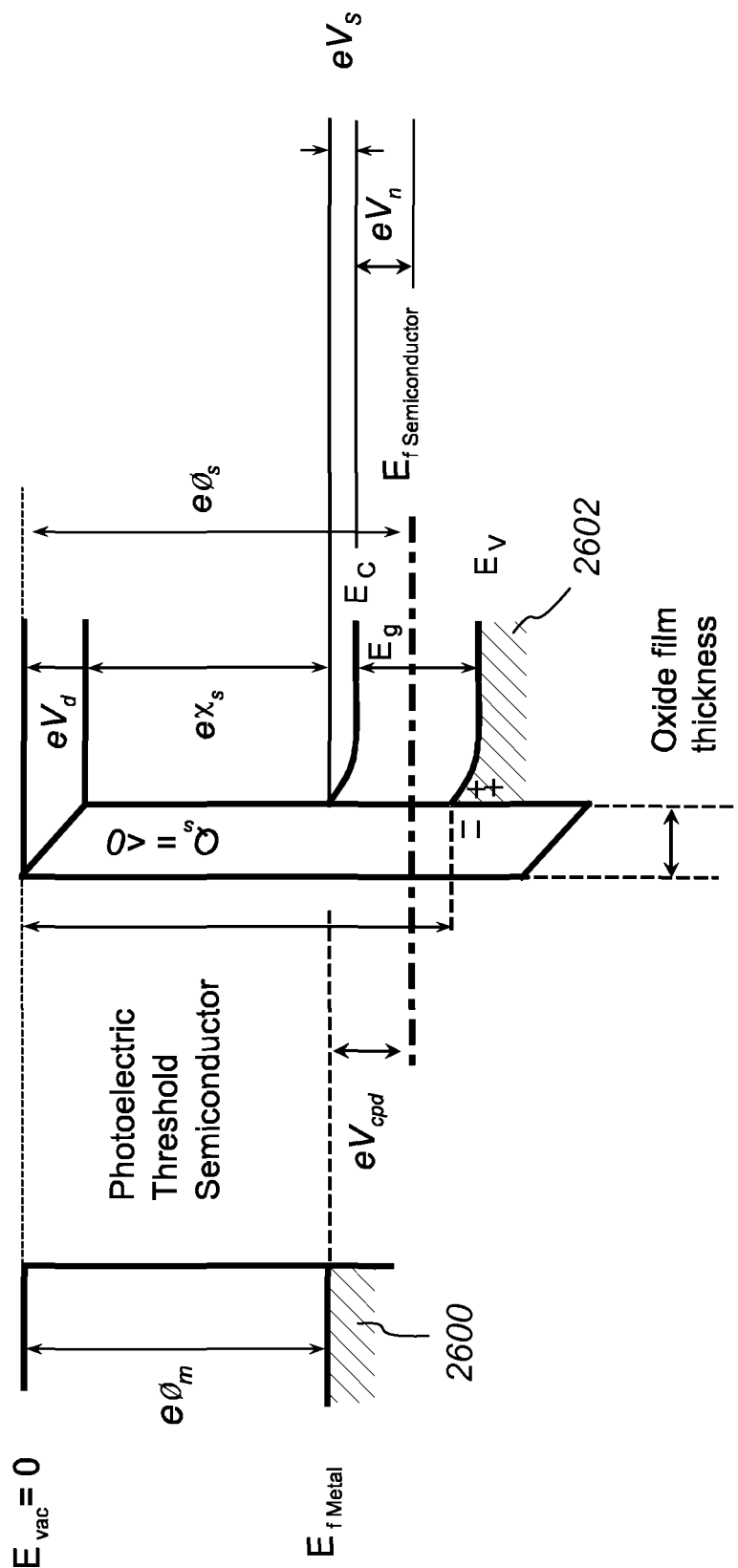
Figure 27:
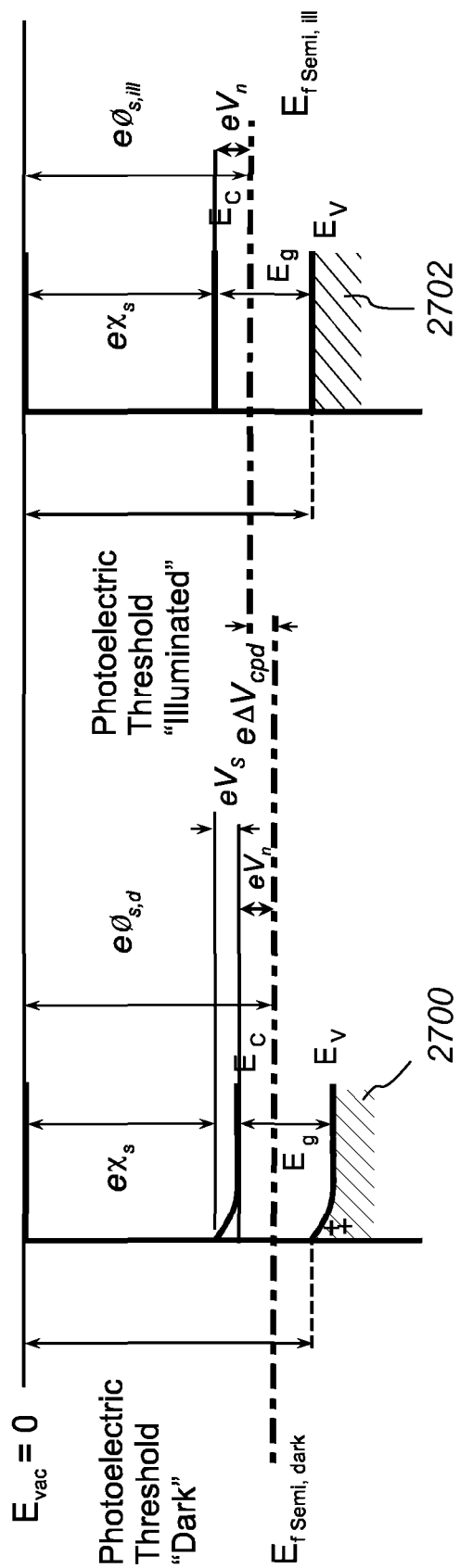
Figure 28:
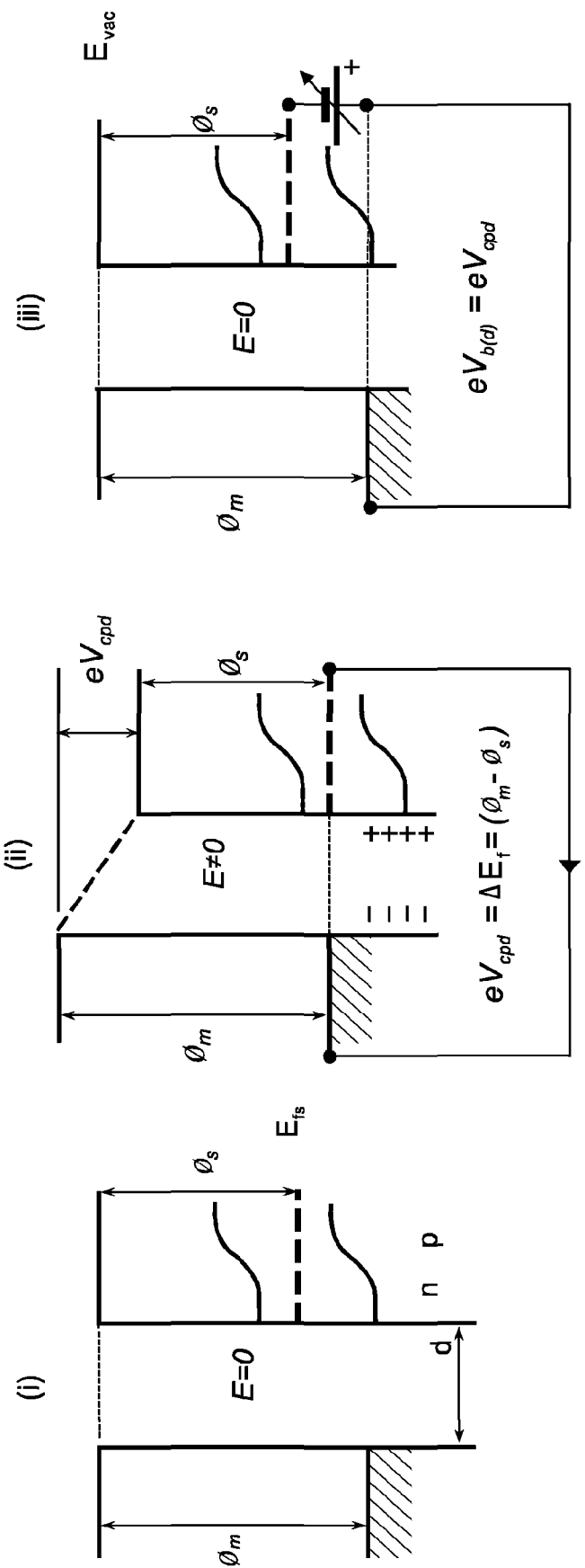
Figure 29:
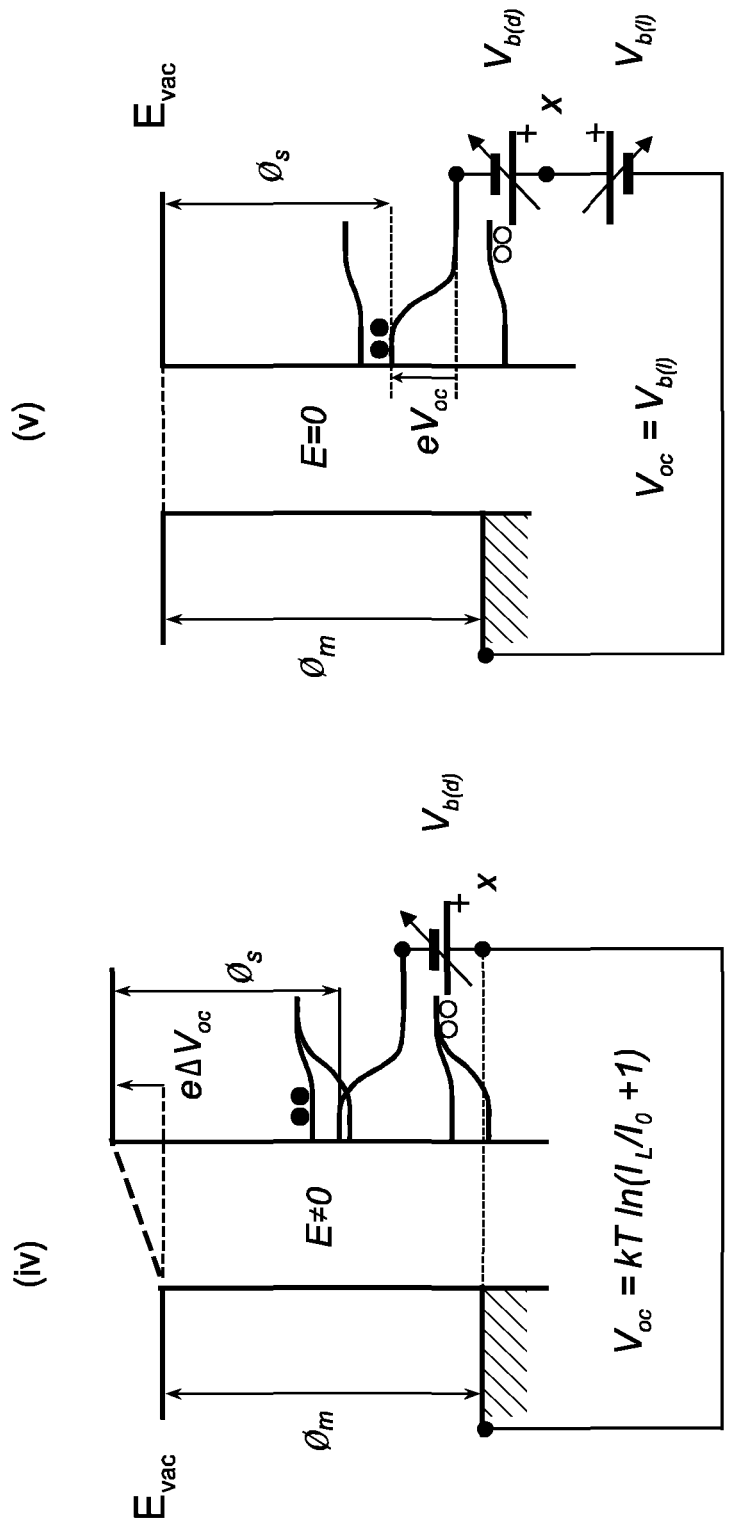
Figure 30:
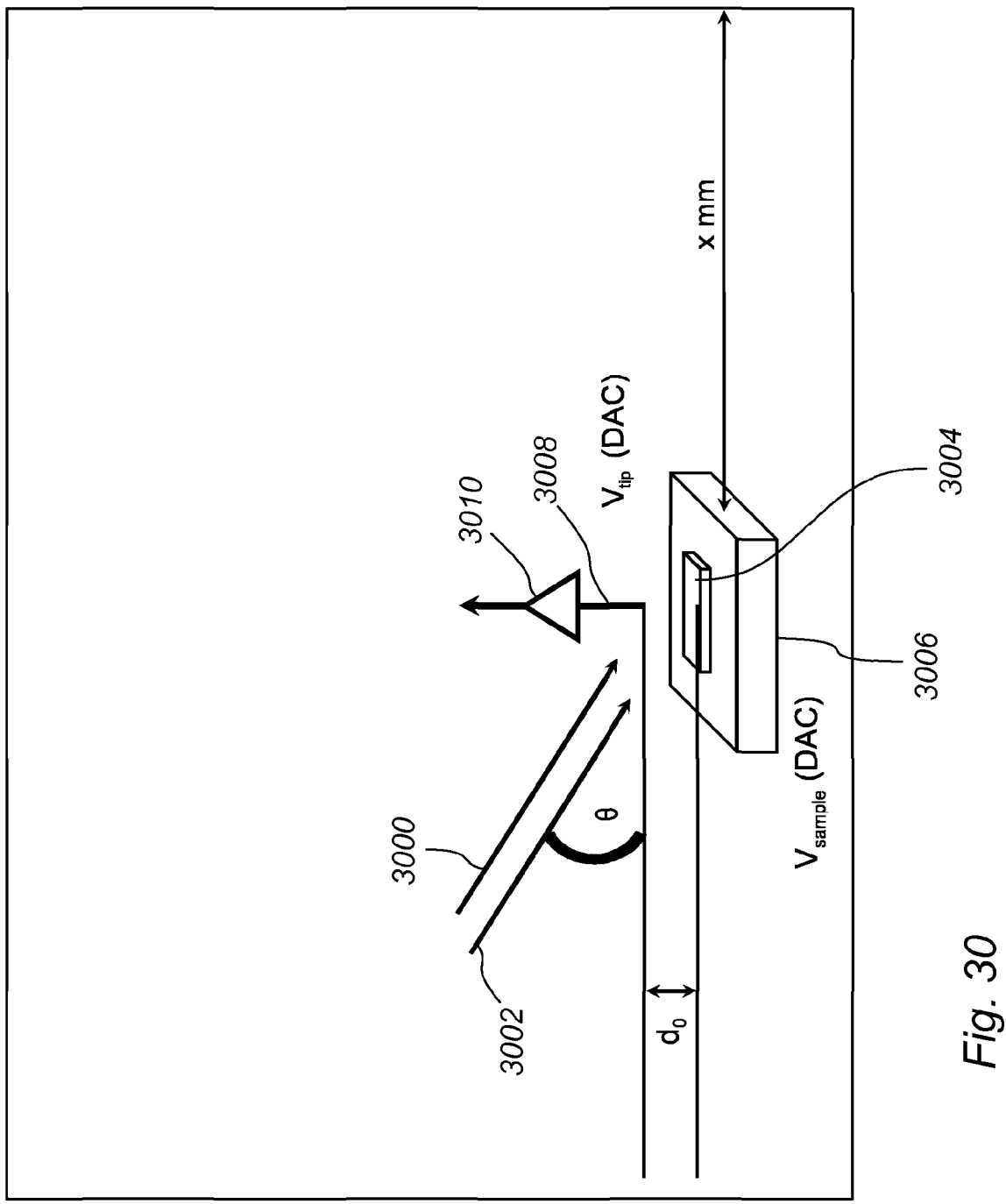
Figure 31:
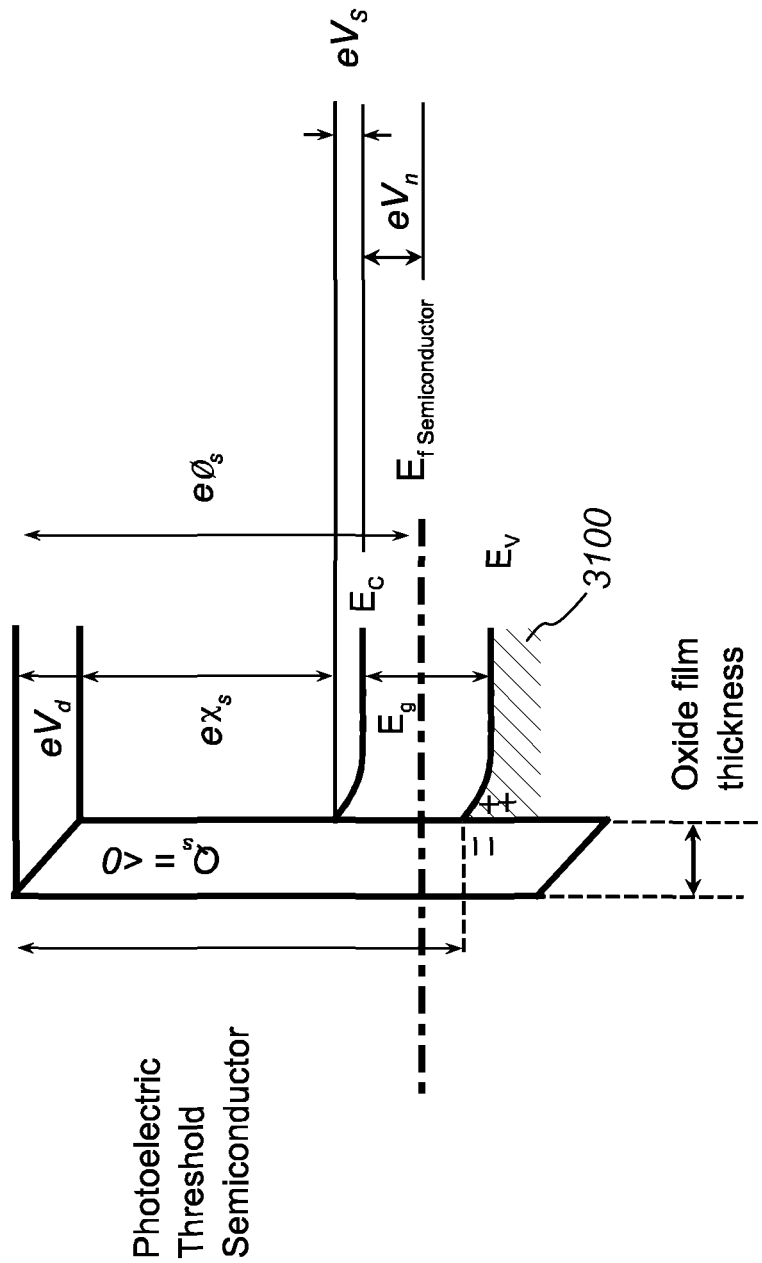
Figure 32:
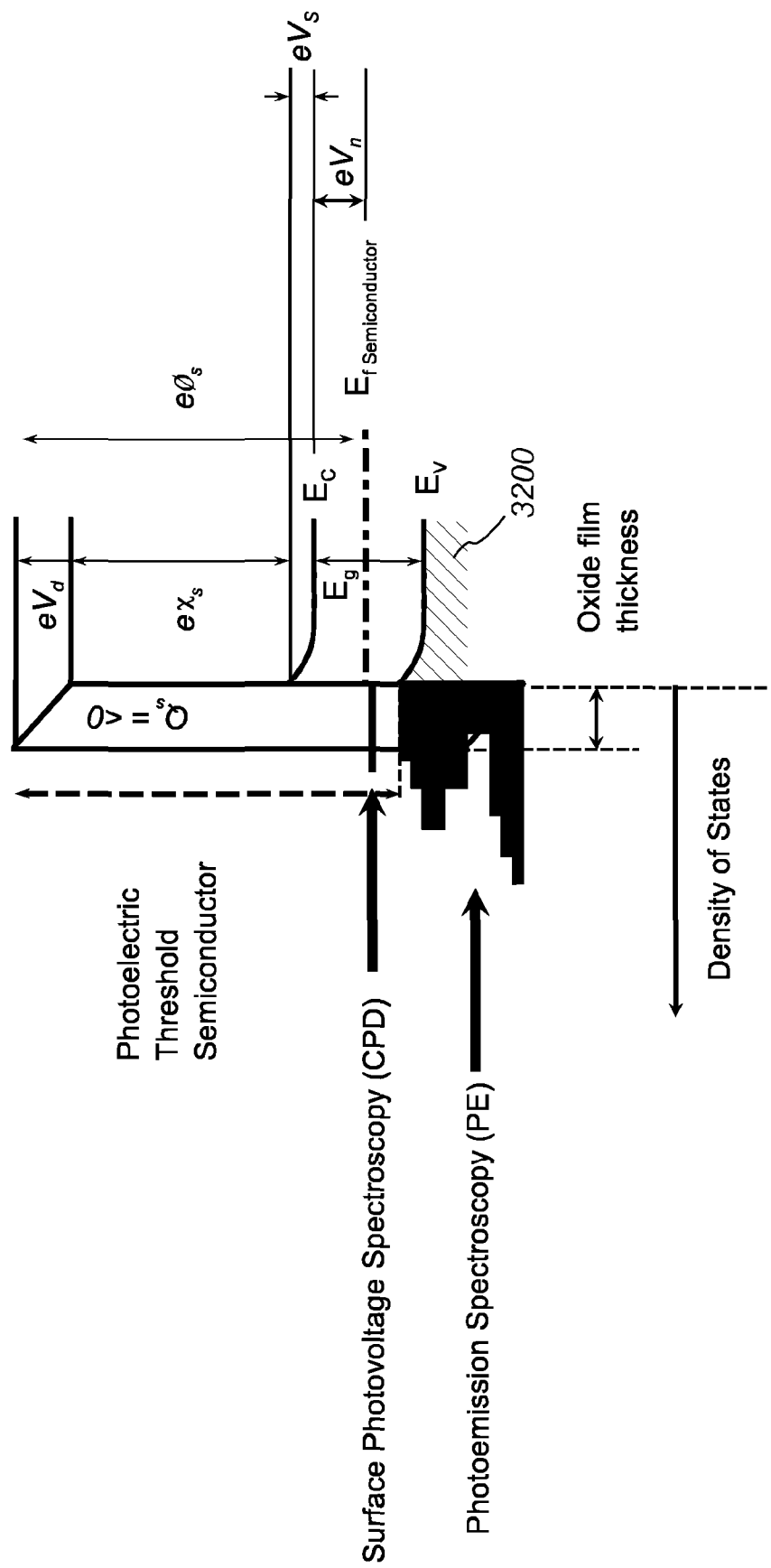

FIG. 11 illustrates aspects of light sources for use in the system of FIG. 10, wherein FIG. 11A shows a broad band UV light source focused into a monochromator type wavelength selector, FIG. 11B shows a similar arrangement where a sample is contained in the light source housing; and FIG. 11C shows an arrangement wherein the sample atmosphere is controlled independently of the atmosphere required or used for the light source, and an appropriate window is provided at a terminating portion of the enclosure for the transmission of light;

FIG. 12 illustrates alternative embodiments of light sources for use in the system of FIG. 10, wherein FIG. 12A shows a broad band UV light source focused into a filter type wavelength selector; FIG. 12B shows a similar arrangement where a sample is located within a light source housing; and FIG. 12C shows an arrangement wherein the sample atmosphere is controlled independently of the atmosphere required or used for the light source, and an appropriate window is provided at a terminating portion of the enclosure for the transmission of light;

FIG. 13 shows examples of discrete rotational interference filters;

FIGS. 14 and 15 show alternative types of filters that can be used;

FIG. 16 illustrates an embodiment comprising multiple light sources;

FIG. 17 illustrates an alternative embodiment comprising a dual light source;

FIG. 18 illustrates a frequency separation characteristic for various different detection modes of a Kelvin probe system equipped with a combined UV and visible/IR light injection system;

FIG. 19 illustrates the gains applied at a detector electrode for air photoelectric emission and also voltages (biasing) of both tip and sample;

FIG. 20 shows approximately two periods of an output signal for a vibrating Kelvin probe which is suspended just above a sample that is being illuminated with a DC UV light beam;

FIG. 21 shows a schematic of an overall control system according to the invention;

FIG. 22 illustrates the definitions of vacuum level, photoelectric work function and fermi level for an ideal clean metal;

FIG. 23 illustrates photoemission for an ideal clean metal sample;

FIG. 24 illustrates an energy diagram for an ideal clean semiconductor;

FIG. 25 illustrates an energy diagram for a semiconductor with an oxide coating and no interface charge;

FIG. 26 illustrates an energy diagram for a semiconductor with an oxide coating and a negative interface charge;

FIG. 27 illustrates an energy diagram for a semiconductor under illumination with an illumination energy being greater than or equal to a band gap energy of the semiconductor;

FIG. 28 illustrates an energy diagram showing aspects of a contact potential difference measurement of a non-illuminated semiconductor PN junction;

FIG. 29 illustrates surface voltage spectroscopy of an illuminated semiconductor PN junction, with an illumination energy being greater than or equal to a band gap energy of the semiconductor;

FIG. 30 illustrates aspects of a measurement apparatus according to an embodiment of the invention; and FIGS. 31 and 32 illustrate summaries of various measurement modes.

Figure 1:
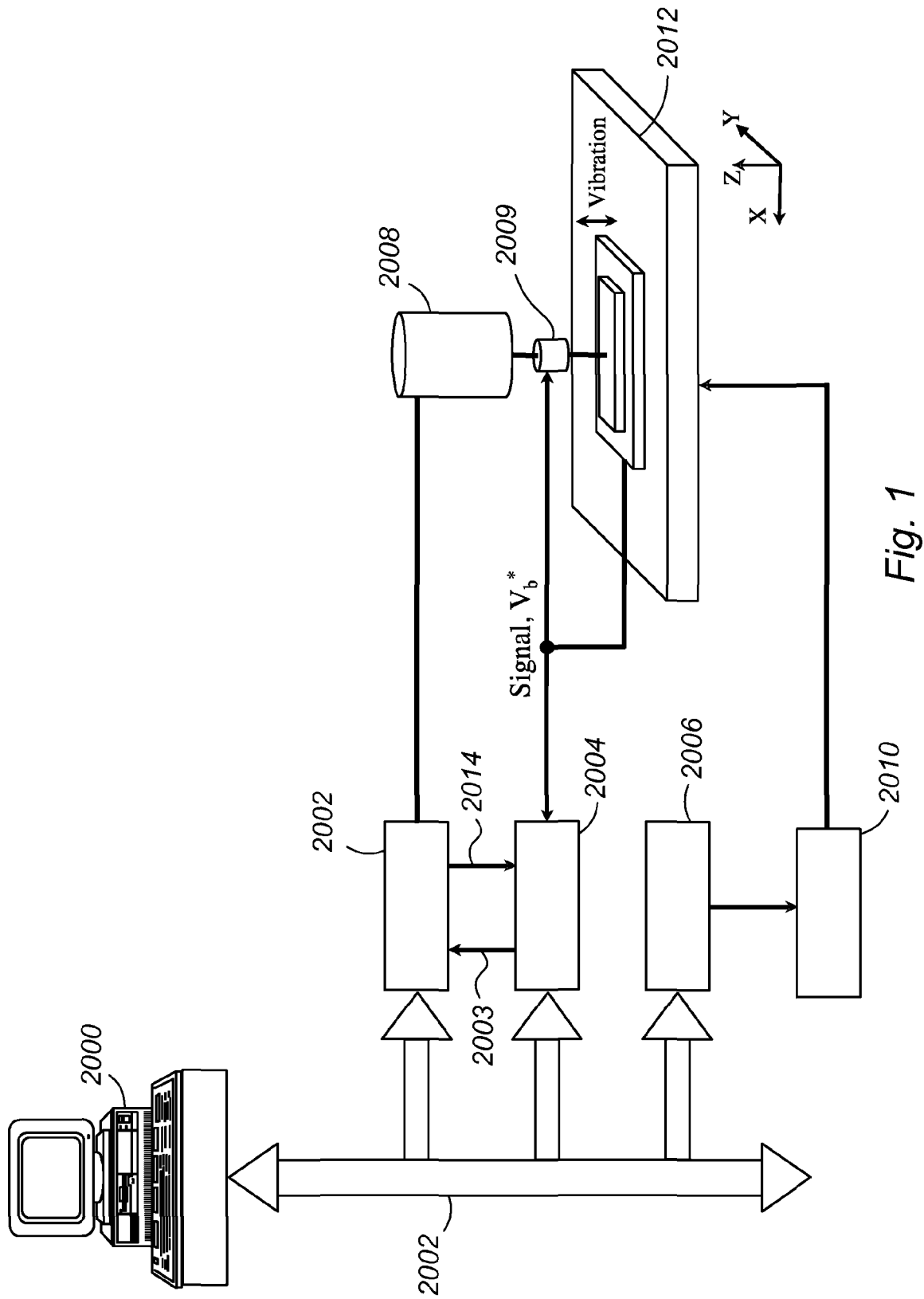
FIG. 1 is a schematic of an existing scanning Kelvin probe arrangement.

An overview of a Kelvin probe system is shown in FIG. 1. A host computer 2000 communicates with various subsystems (2002, 2004, 2006) via a data bus (example: XT/AT). A digital oscillator 2002 sets the frequency of a voice coil 2008, amplitude, and probe trigger signal 2003. The voice coil 2008 drives the vibration of a I/V converter and tip 2009. A data acquisition system (DAS) 2004 (example: based upon the National Instruments PCI-1200 board, or PCI-6025E National Instruments card) measures a peak-to-peak (ptp) output signal $V_{ptp}$ as a function of a backing potential $V_b$, and sample translation (x, y and coarse z) is controlled via a parallel-port interface 2006, which sends control signals to a stage driver 2010 which moves the sample stage 2012.

The backing voltage can be connected to either sample or tip so the sample is therefore mounted on an insulator to accommodate either configuration. The trigger signal is used to synchronize data acquisition so that the DAS 2004 can measure, at relatively high frequencies (around 10-40 kHz), the portion of the signal corresponding to the peak-to-peak height. This is accomplished by setting a variable delay derived from the digital oscillator 2002. Application of a DC offset 2014, via a 12-bit digital-to-analog converter (DAC) (provided at the DAS 2004) permits high accuracy (40 nm) probe vertical positioning. A three-axis microstepper positioner (example: AMSI Corp. 6006), coupled with linear translation stages (example: Newport 460XYZ) can permit macroscopic sample positioning (0.4 μm/step). The scanning system can perform linescans or topographies in the range of 200 μm up to 30 cm or more on a side.

Figure 2:
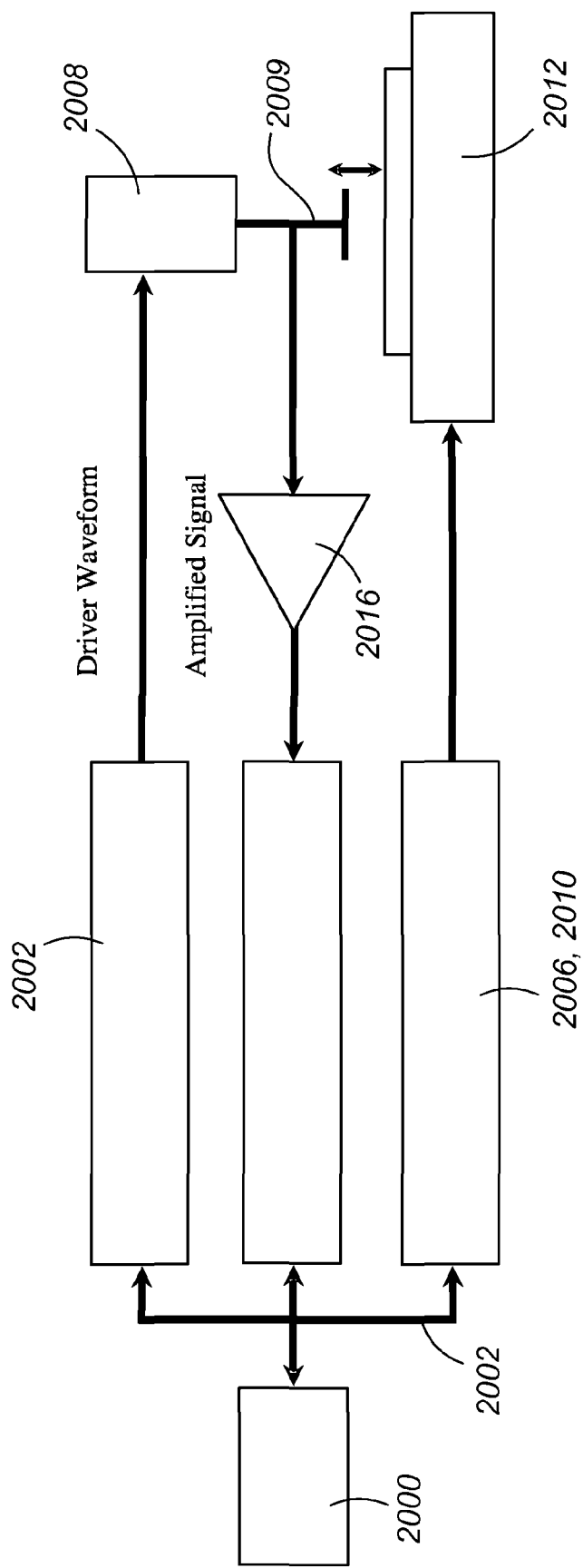
FIG. 2 is an alternative schematic illustration of a similar system.

FIG. 2 is an alternative schematic illustration of a similar system, in which like components are illustrated with like reference numerals. Amplification 2016 of the probe signal is also illustrated (this may be present in the arrangement of FIG. 1 also).

Figure 3:
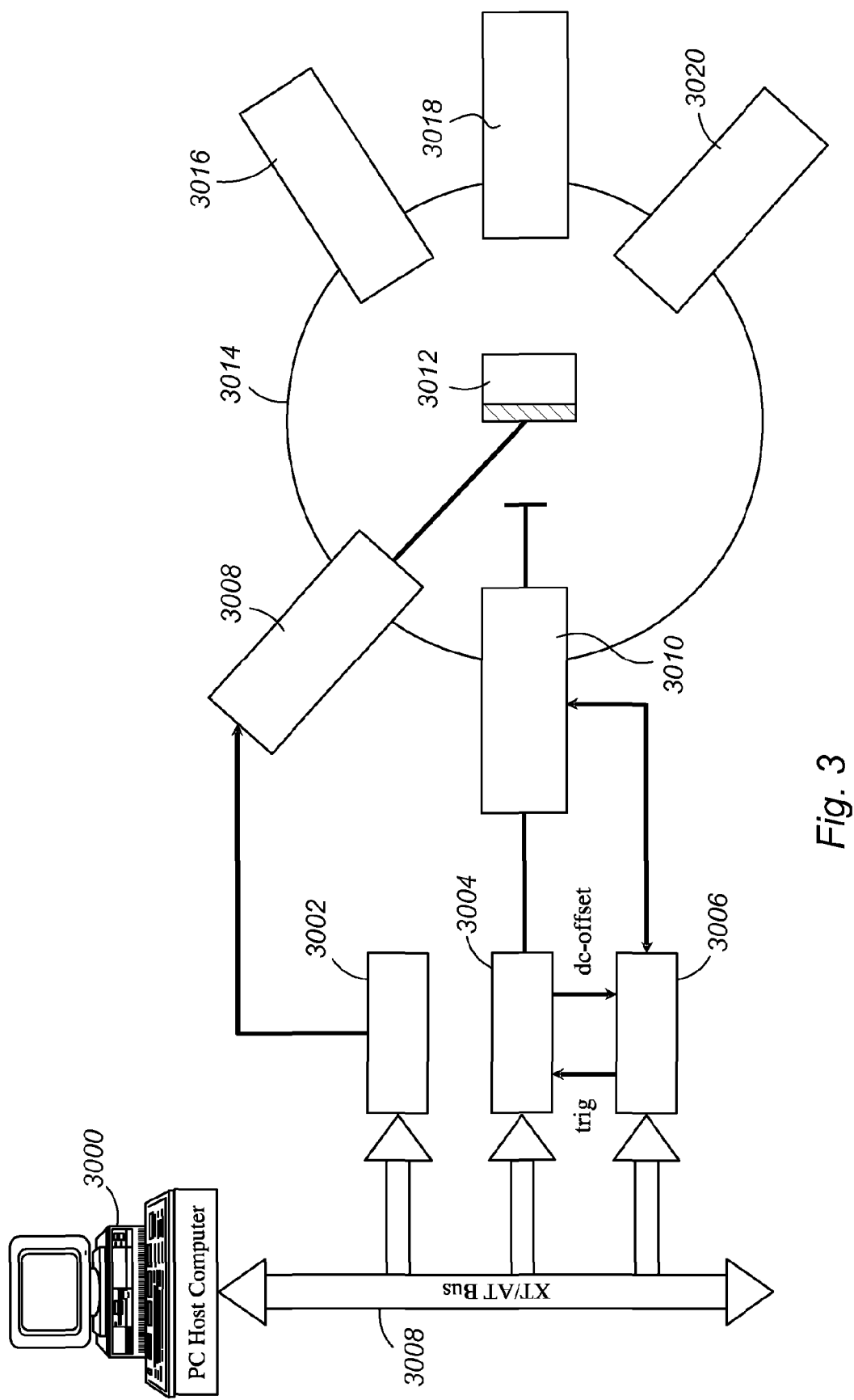
FIG. 3 shows an example of an ultra-high vacuum (UHV) PE measurement system.

FIG. 3 shows an example of a PE measurement system, in which a Kevin probe 3010 is used in an ultra high vacuum (UHV) environment as the detector for a photoelectric spectroscopy system. A host computer 3000 communicates with various subsystems (3002, 3004, 3006) via a data bus 3008 (example: XT/AT). Power unit 3002 is provided for a light source 3008. Kelvin probe 3010 is controlled by a digital oscillator 3004 and is connected for two-way data transmission with a data acquisition system and DAC 3006. The sample, sample holder and sample heater (assembly 3012) are housed within an ultra-high vacuum (UHV) enclosure 3014. Other instrumentation for carrying out the PE measurements includes ion gauge 3016, cold finger 3018 and mass spectrometer 3020.

Figure 4:
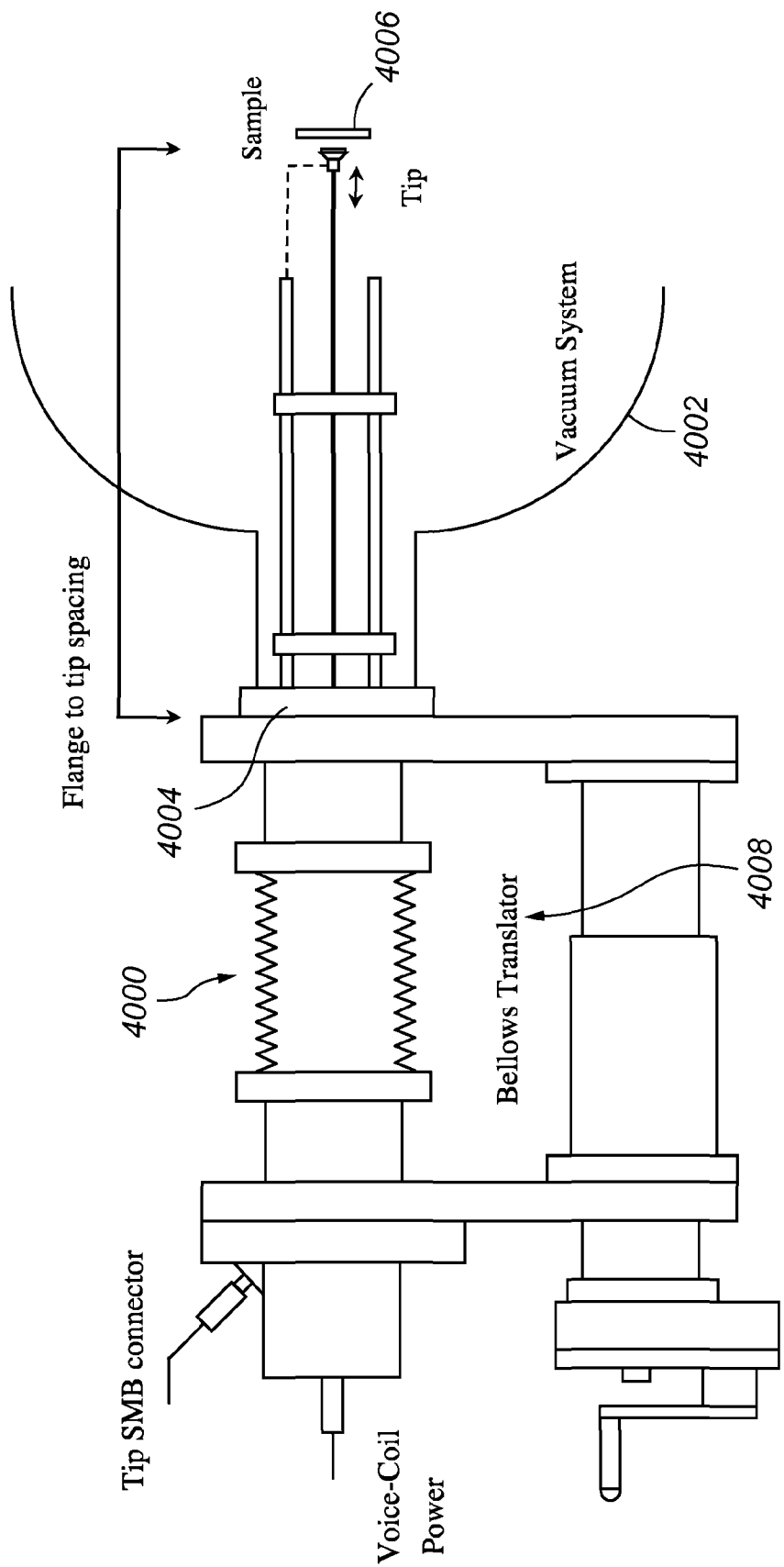
FIG. 4 shows details of a UHV Kelvin probe head as used in the system of FIG. 3.

FIG. 4 shows some further details of the UHV probe head for Kelvin probe 3010 as used in the system of FIG. 3. A UHV Kelvin probe 4000 is mounted on a UHV chamber 4002 via a 2/3/4 inch OF flange 4004. Also mounted is a sample holder/sample heater on a (x,y,z) stage (assembly 4006). The UHV chamber 4002 is equipped with a PE source, such as a QTH lamp which illuminates the sample via a quartz view port. The UHV Kelvin probe 4000 is mounted on a 100 mm manual translator 4008 comprising a bellows and an actuator. The base pressure of the UHV chamber is <1E$^{-10}$ mBar and the residual gas composition will be $H_1$ and $H_2$ (80%), CO (5%), $CO_2$ (5%), and miscellaneous other gases (10%). The mass spectra are monitored using a 0-300 amu mass spectrometer. The system pressure is monitored using a nude ion-gauge.

This system can be used to monitor the photoemission for Cs layers deposited upon various metal samples. As the work function of Vs is low <2.0 eV then visible light can be used. Alternatively for sample of work function under 4.8 eV a Mercury source can be utilised.

Figure 5:
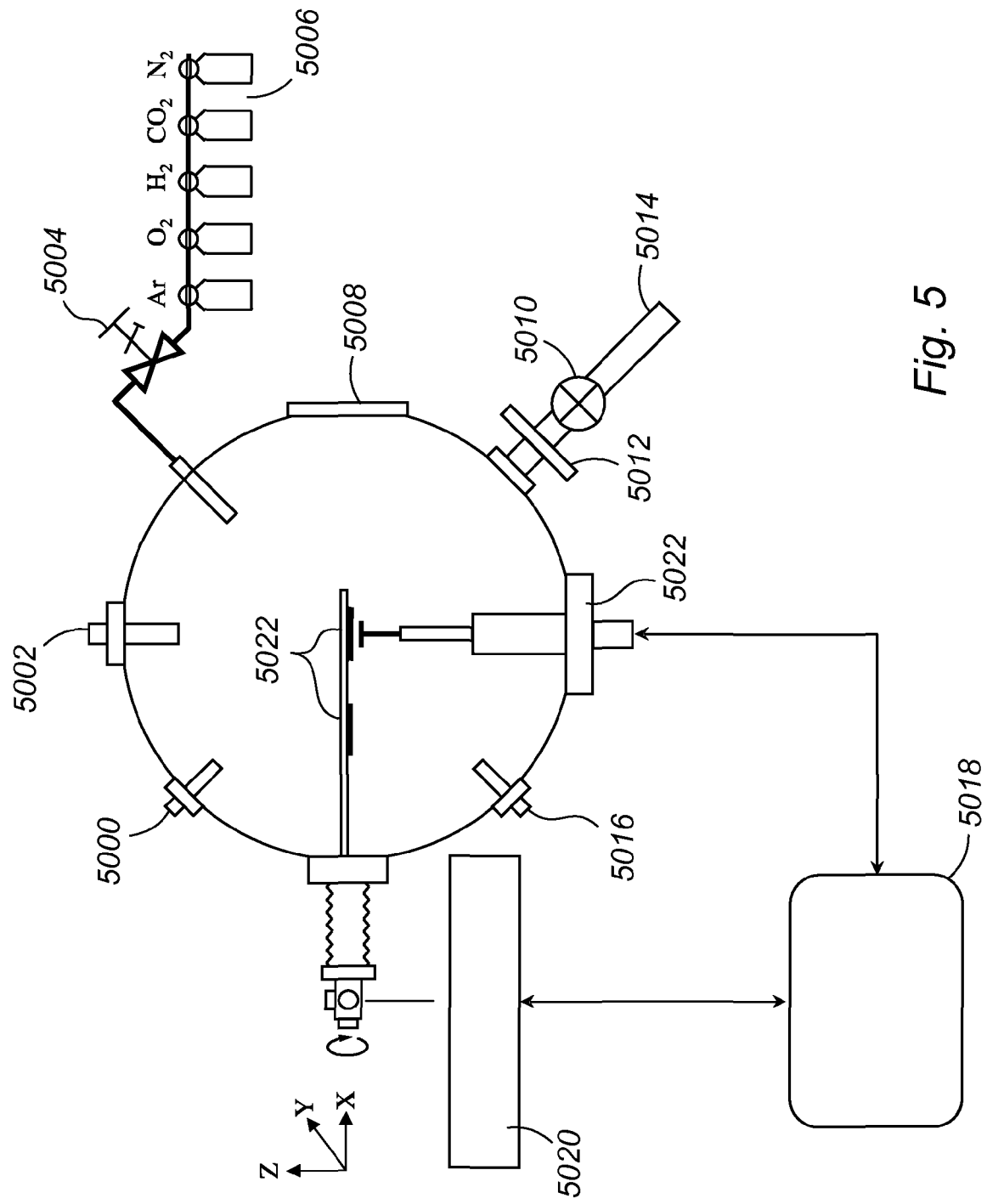
FIG. 5 shows a further example UHV PE system.

FIG. 5 illustrates a further example UHV system. This system is used for measuring the work function of the tip of a Kelvin probe, rather than measuring the work function of a sample itself. A person skilled in the art will be able to appreciate from the figure how the system functions. The system comprises the following components: Quadrupole Mass Analyser 5000; E-Beam Evaporator 5002; Pulsed Nozzle Valve 5004; Gas Inlet System 5006 for inlet of Ar, $O_2$, $H_2$, $CO_2$, $N_2$; Fast Entry Load lock 5008; Hg, Zn, Cd Spectral Lamp 5010 with 312.6 nm Bandpass Filter 5012 and Optical Rail 5014; Ion Gauge 5016; Host Computer 5018; and X-Y-Z Translation Stage 5020. Samples 5022 are arranged and are moveable to be detected by probe 5022. The probe 5022 can be a PE probe with I-V Converter and Pre-Amplifier or a (scanning) Kelvin Probe with Probe Oscillator, Pre-Amplifier, AD Converter, DA Converter.

Figure 6:
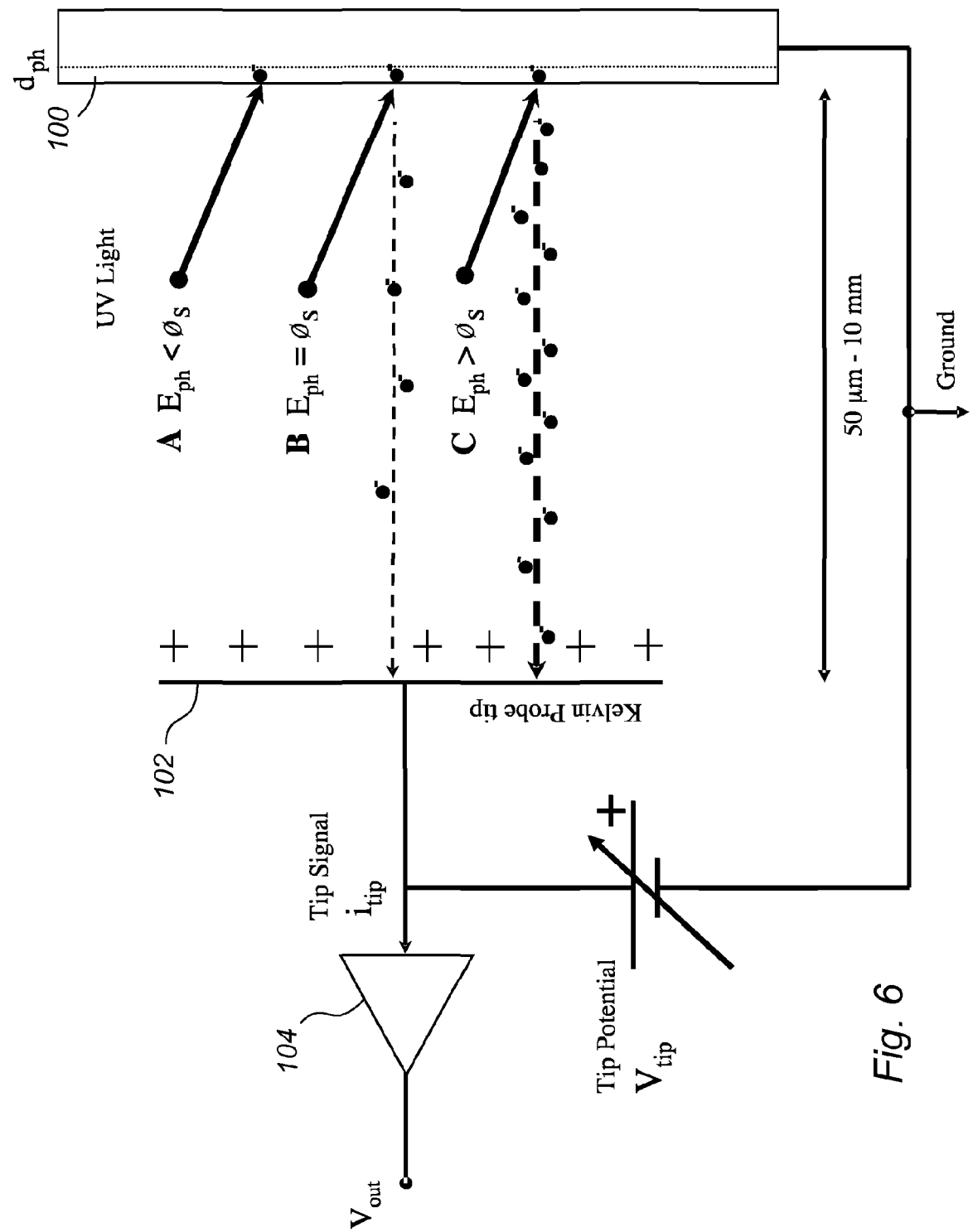
FIG. 6 is an explanatory diagram illustrating various selected aspects of photoelectric emission.

FIG. 6 shows three light beams (A, B and C) incident upon a conducting sample 100 which has an associated work function $\Phi_S$. Each light beam A, B, C represents a different illustrative scenario. The maximum penetration depth of the photons into the sample surface is denoted by $d_{ph}$. The photon energy is described by $E_{ph}$=hf, where 'h' is Planck's constant (6.626×10$^{-34}$ Js) and 'f' is the frequency of the light in Hertz. A metallic electrode 102 is provided for the detection of emitted electrons. The metallic electrode 102 may for example be a Kelvin Probe tip.

The sample 100 and the tip 102 may be in a vacuum, in which case they are contained within an evacuated housing. The quality of a vacuum can never be absolutely perfect. As used herein a "vacuum" is present whenever a dedicated vacuum pump or system is provided. The vacuum may in certain embodiments be a so-called ultra-high vacuum (UHV) which may have a pressure of say 10$^{-7}$ Pa or lower; but other less perfect vacuums fall within the meaning of "vacuum" in the present context.

Alternatively, the sample 100 and the tip 102 may be exposed to or housed within a gaseous environment. This is present whenever a dedicated vacuum pump or system is either absent or switched off. The gaseous environment may be the ambient atmosphere (air) which may be equal to, less than or greater than atmospheric pressure, or may be a gas with a controlled relative humidity, or be a controlled gas such as $N_2$. These are mentioned as examples only. The type of gaseous environment that is used will depend on the requirements of the specific application of concern.

The special case of air does not require a separate housing to provide the necessary atmosphere, although in practice a housing may be provided to shield the sample from unwanted electromagnetic interference or other signals. In general, if a controlled gas or a gas with a controlled relative humidity is used a housing will be provided for sample 100 and tip 102 to provide the environment. It would be possible though in some cases to control the environment of a room containing the equipment using HVAC or other environment controls, so that the atmosphere between the tip and the sample can be controlled globally without having to provide a separate enclosure and associated control mechanisms for manipulating the enclosure's environment.

In the case of beam 'A' the photon energy is smaller than the work function of the sample $\Phi_S$ and any excited electrons do not have sufficient energy to leave the material so there is no contribution to the detected current at the Kelvin probe tip 102. In example implementations, the Kelvin probe tip 102 may be spaced 50 μm-10 mm away from the outer surface of the sample 100. One particular tip, mentioned herein as an example only, has a diameter of 1.8 mm diameter and is located 1-3 mm away from the sample 100.

In the case of beam 'B' the photon energy is equal to the work function of the sample $\Phi_S$ which means the beam does have sufficient energy to liberate photoelectrons from the surface of the sample 100. Once free of the surface fields (extending some tens of nanometers from the surface), such electrons are then subject to any electrical fields between tip 102 and sample 100.

In the case that the tip potential $V_{tip}$ is zero, then the electrons (and any air/gas molecules they are attached to) will drift according to the field created by the contact potential difference (CPD) (or work function difference) between sample 100 and tip 102, i.e. $eV_{cpd}$=e($\Phi_s$-$\Phi_{tip}$), where 'e' is the electronic charge and $\Phi_s$, $\Phi_{tip}$ are the work function of the sample 100 and tip 102 respectively. As an example, in a case where the sample 100 is Gold with work function 5.1 eV and the tip 102 is Aluminium with work function 4.0 eV, then the voltage difference between tip 102 and sample 100 will be 1.1 Volts with the tip surface being positively charged and the sample surface being negatively charged. Electrons will be attracted to the positive tip 102 and constitute an electronic current which is amplified via amplifier 104 and output to a data acquisition system (DAS), which receives the output voltage $V_{out}$. In cases like this where the work function of the tip 102 is less than that of the sample 100, photoelectrons will drift to the tip 102. However, if the work function of the sample 100 is greater than that of the tip 102, then the field is reverse-biased with respect to the negatively charged electrons and no current will be detected.

In the case of beam 'C' the energy of the photons is sufficiently high to liberate a large number of electrons and some will exit, or be ejected, with considerable kinetic energy (KE), following KE=($E_{ph}$-e$\Phi_s$). As the energy is now higher than the sample work function an energy distribution of electrons results, corresponding to electrons at the highest energy in the sample—the Fermi energy—being ejected with the maximum KE and other electrons, perhaps located a distance underneath the surface at an energy below the Fermi level, being ejected with less or even zero KE. An energy analysis of these ejected electrons would show that the number of ejected electrons is linear with the square root of the difference between the energy level the electrons occupied in the sample and the Fermi level. This electron distribution is termed the sample density of states or DOS(Sample) and it acts as a 'signature' of the material and its surface condition.

Thus in FIG. 6 Beam 'C' contributes the most to the output current, with the characteristics of that current depending upon the energy of the incoming photon and DOS(Sample).

A full description of the photoelectric emission would also take account of the contact potential difference existing between tip 102 and sample 100 and the DOS of both the sample and the tip (See FIG. 7 below). In the case that the tip potential $V_{tip}$ is quite large, say 5-10 Volts, and positive with respect to the sample 100, then this will dominate over any CPD between the two surfaces, whether they be reversed biased by their CPD or not. In general this is the condition used to measure the photoelectric emission effect, as a function of incoming photon energy.

Figure 7:
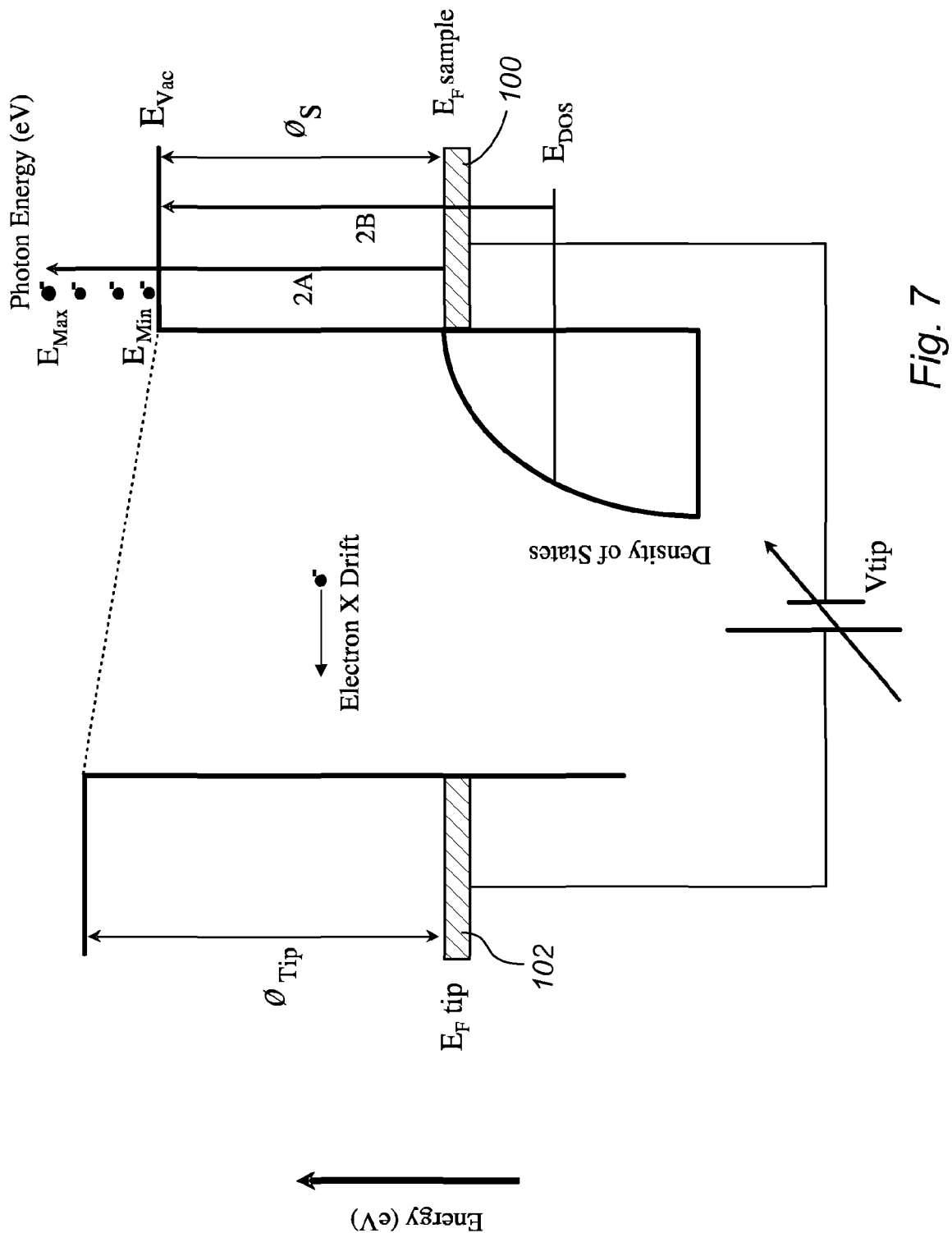
FIG. 7 illustrates an electron energy diagram for a sample and a detector electrode of the arrangement shown in the explanatory diagram of FIG. 6.

FIG. 7 shows an electron energy diagram of the sample-tip arrangement of FIG. 6. The diagram shows electron energies plotted on a vertical scale, with representations of the sample 100, electrode 102 shown. Here the sample 100 is illuminated by a beam of light having a photon energy greater than the sample's work function $\Phi_S$, which is defined as the energy difference between the Fermi level, $E_{F\;sample}$, which represents the highest occupied energy level, and the vacuum energy level, which in this example is called $E_{vac}$. The incoming photons can eject an electron at the Fermi level to a position above $E_{vac}$, shown as transition '2A'. Provided the incoming photon has sufficient energy, it can promote electrons at an energy level within the surface density of states (EDOS) to the $E_{vac}$, represented by transition '2B'. Other transitions between '2A' and '2B' are also possible.

FIG. 7 shows an example where the Fermi levels of the sample and tip are co-aligned. In a case where the tip work function is greater than the sample, electrons have to drift across the intervening space to arrive at the tip. Only those electrons having suitable energy greater than the work function difference will arrive and thus constitute the tip current.

If the energy of the incident photons is constant at an energy sufficient to liberate electrons from the surface density of states then electrons are ejected with a range of kinetic energies. The kinetic energy for electrons from a given state is determined by the difference between the energy of the incident photon and the energy difference between the electronic state and the vacuum (greater than or equal to the work function).

Electrons traversing the gap between sample and tip can be stopped by adjusting the tip potential such that the $eV_{tip}=K_{max}$, where e is the electronic charge and $K_{max}$ is the kinetic energy of the electron. This is known as the stopping potential and is the potential required to just stop electrons arriving at the tip. This equation holds true for a vacuum. In air (or similar gaseous environment), the kinetic energy of the electrons is lost due to the collisions with air molecules.

To observe the energy spectrum of the ejected electrons the tip potential can be controlled to vary through a voltage range, between say −10 to +10 Volts, in small voltage increments thus stopping all electrons below each selected energy. The current as a function of limiting energy is the integral of the energy spectrum of the ejected electrons. Therefore to recover the energy spectrum the derivative of this measurement is taken. Deriving the energy spectrum in this way, measuring the integral of the energy spectrum of the ejected electrons, is different from existing techniques which measure the electron energies by acceleration rather than stopping potential in which case they measure the electron energy spectrum directly. This is a new type of photo-electron spectroscopy termed Kelvin probe Air Photoelectron Spectroscopy (KP-APS).

It is also possible to perform Angle Resolved Photo-Electron Spectroscopy (ARPES). Electrons with low kinetic energy can only escape in the direction normal to the sample surface, whereas high kinetic energy electrons can escape at large angles from the normal to the surface. ARPES measures electrons as a function of angle.

Figure 8:
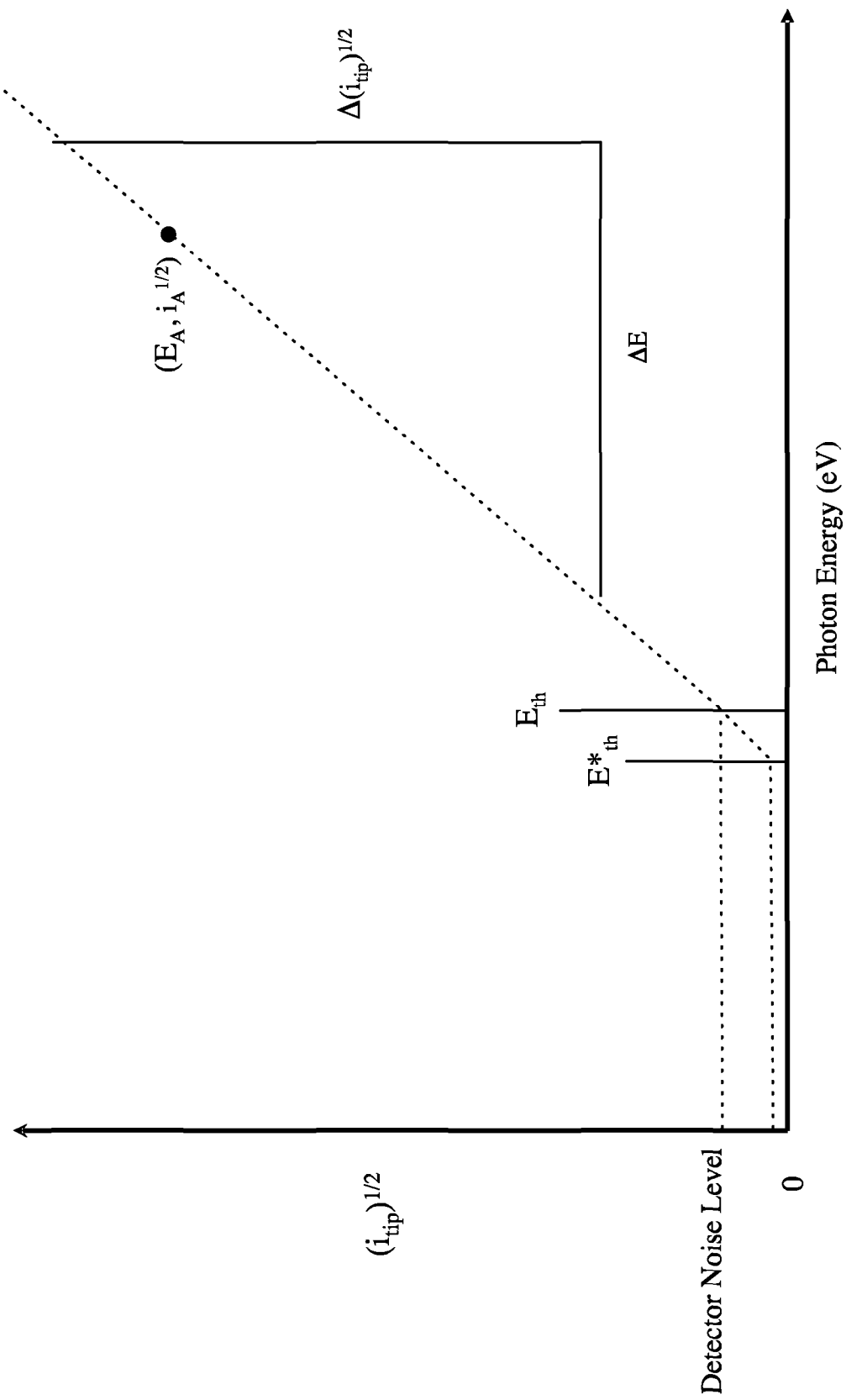
FIG. 8 illustrates an ideal air photoemission characteristic for metals, showing the square root of the photoemission current in a detector electrode as a function of incoming photon energy, for the type of arrangement shown in FIGS. 6 and 7.

FIG. 8 depicts an ideal air photoemission characteristic, showing the square root of the photoemission current $(I_{tip})^{1/2}$ as a function of incoming photon energy. As the theoretical relationship of the number of electrons at a particular energy level $E_{DOS}$ (see FIG. 7) in the Density of States at electron energies below $E_F$, varies as $E^{1/2}$ where E represents $(E_F - E_{DOS})$ then we anticipate a linear output after the threshold $(E_{th})$ corresponding to $\Phi_S$. The threshold position is normally represented as the intersection of the average detector noise level for photon energies below $E_S$ with the line representing the electron yield. The gradient of the electron yield is $\Delta(I_{tip})^{1/2}/\Delta E$, where $\Delta E$ represents a photon energy difference and $\Delta(I_{tip})^{1/2}$ the associated change in photoemission current.

It is to be appreciated that the air photoemission characteristic of FIG. 8 is an example only. The variation of the number of electrons with E will vary according to different powers according to the type of sample material. The power of ½ shown in FIG. 8 applies in the case of metals. However, the power may be different (for example ⅓) for other materials. The power may be different for different semiconductors. Whichever power happens to apply for a given sample, the y-axis showing the photoemission current can be scaled according to that power to produce a linear electrical yield gradient.

As the photon energy is increased beyond the work function of the sample, additional electrons from sub-surface states are detected. This has the effect of modifying the gradient of the photoemission current as a function of photon energy. The gradient changes because the detected yield is the integral of the available states hence the density of states can be recovered by taking the derivative (gradient) with respect to photon energy.

The light beams provided by the illuminator can be either constant intensity (DC) or modulated (AC). In the latter case the $(I_{tip})^{1/2}$ parameter represents the peak-to-trough value of the signal intensity. If the optical chopper is designed to produce an external 'trigger' pulse representing a constant-phase time signal then the data acquisition system can acquire the peak-to-peak current data in a selective window averaging fashion (using for example a boxcar or phase filtered integrator), thus offering a high signal-to-noise (S/N) ratio.

Further if the positions of the peak and trough are recorded at a high signal level, denoted by position $E_A$, $i_A^{1/2}$ in FIG. 8, then this phase information can be utilised to substantially reduce the effect of the noise resulting in a reduced detector noise level and a more accurate reporting of the intersection at $E^*_{th}$ and thus an improved absolute sample work function value. This correction method increases the accuracy of photoemission measurements performed in air/gas.

Figure 9:
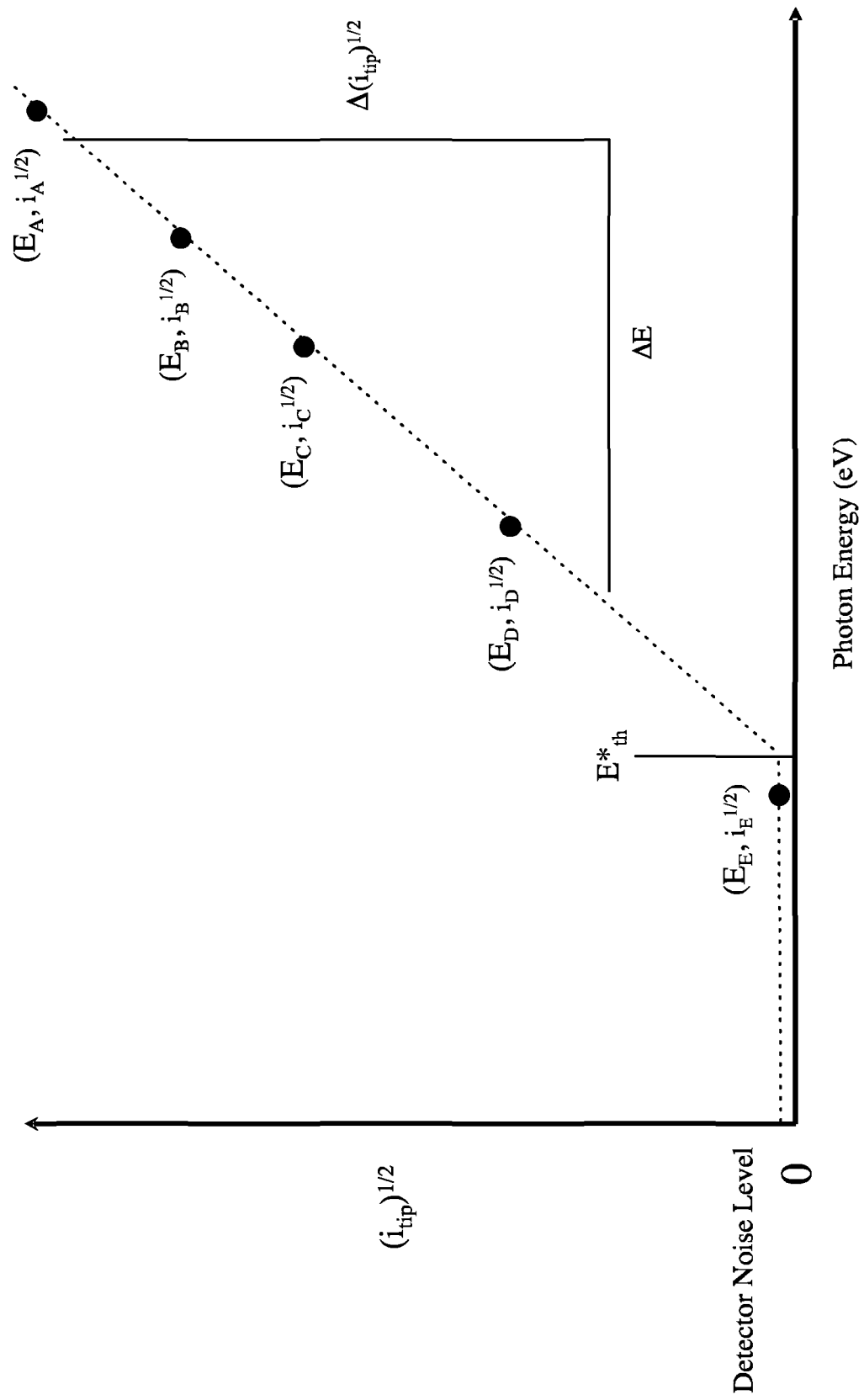
FIG. 9 shows air photoemission characteristics for metals of an 'Off-Null' approach to photoemission measurements.

FIG. 9 shows air photoemission characteristics of an 'Off-Null' approach to photoemission measurements.

In a Kelvin probe, the work function difference between the sample and the tip is equal and opposite to the DC potential necessary to produce a zero or "null" signal, namely the "balance point" at which the Fermi levels are brought level by adjusting $V_b$ to equal $-V_{CPD}$. In an off-null technique, the balance point is not measured directly, but rather it is determined by a linear extrapolation.

An example of the application of an off-null technique to the new system is shown in FIG. 9. Here, the electron yield is measured at a number of different photon energies, say 2-4, above the threshold, corresponding in the Figure to the set $\{(E_A, i_A^{1/2}), (E_B, i_B^{1/2}), (E_C, i_C^{1/2}), (E_D, i_D^{1/2})\}$ and one photon energy $(E_E, i_E^{1/2})$ either below the threshold ($E_{th}$ for DC; $E^*_{th}$ for AC) or with the incoming beam prevented from interacting with the sample, for example by using an optical shutter. This characteristic can be performed under either constant intensity (DC) or modulated (AC) illumination and in the latter case the more accurate $E^*_{th}$ measurement can be deduced for ($E_D$, $i_E^{1/2}$).

The corrected noise level will remain constant for a given system. Therefore the noise value can be stored and used without re-measurement in subsequent calculations. The set of different photon energies can be measured quickly or even quasi-simultaneously. In the above example where five sets are measured (EA through EE) it may be possible to make between 6-20 sets of measurements per minute. This allows changes in the photoelectric threshold (and thus $\Phi_S$) to be followed more closely, that is, more frequently, than in existing systems.

To detect the photoelectric threshold the energy (wavelength) of the primary light beam is scanned. This can be done from a lower to a higher energy or vice-versa. The advantage of the former is that the sample is only exposed to potentially damaging photons for the minimum time. The energy dependent negative ion current $I_{nic}$ can be adjusted for differences in relative source intensity, i.e. normalised for a constant light flux, then the data set of $[(I_{nic})^{-1/2}, E_{ph}]$ shown in FIG. 9 permits determination of the detector noise level and a straight line describing the yield.

Further mathematical analysis can be applied to the data set to achieve a best-fit straight line (on the yield data above the photoelectric threshold), resulting in three output parameters: the intersection of the photoelectric threshold, the gradient of the yield and $R^2$, where R is the Pearson correlation coefficient and is typically in the range 0.85-0.99.

The above measurement process typically takes 1-2 minutes on a 50-point wavelength data set. This can considerably reduced if only 2-3 points were recorded on the yield curve and the background was recorded every say 5-10 data sets. This allows a previously unsurpassed rate of determination of photoelectric threshold (photoelectric work function) of say 0.4 Hz, yet retaining a high photoelectric work function resolution.

Repeated measurement of photoelectric threshold using this system give accuracies of 10-20 mV.

Aside from recording time-dependent phenomena, using rapid switching multiple UV sources (see FIG. 16) or rapidly rotating filters (see FIG. 13B) allows for real-time work function tracking, and the possibility of conducting sample 1D linescans or 2D sample work function topographies. As the work function data can now be averaged and the standard deviation calculated the resulting error will be less than in existing PE systems. It has been determined that an achievable error reduction is a fall from an error of 0.050-0.100 eV to 0.010-0.030 eV.

The photo-emission current from the sample detected at the tip can be increased if the sample is negatively biased, for instance −30 to −70 V or higher. This may be accomplished by providing two Digital to Analogue (DAC) converters, one for the tip and one for the sample, as indicated in FIG. 30. It is also possible to reduce or eliminate the photo-electron current if the electrical potential of the sample is made positive with respect to the tip.

During this procedure it is likely that photons of UV light will impinge on the metallic tip creating an electron cloud around the tip. As the potential of the tip is positive then these electrons are immediately re-adsorbed producing no net change to the measured current. However if the tip potential is maintained at a negative value, e.g. −10V then a photon-energy scan would produce the photoelectron threshold of the tip surfaces involved in the interaction, i.e. the face and sides of the tip. The contribution from the tip sides can be minimised by reflecting the illumination beam from the sample surface such that only the tip face is involved. No photoemission current from the sample would be detected as any charged atmospheric ion originating at the sample surface would be would be repelled by the electric field between tip and sample.

Differentiation of the light intensity corrected $I_{nic}$ data with respect to photon-energy will produce information of the shape of the energy bands (valence) from which the electrons have been ejected. FIG. 32 shows filled energy states below the valance band maxima (VBM). Provided the incident photon energy is sufficient these states will contribute to the 'cloud' of emitted electrons and will consequently be collected as an atmospheric ion current at the tip. Thus the tip current represents a photon-energy convolution of the density of states below the VBM.

This off-null, AC technique constitutes a new, much faster and more accurate measurement mode of Photoelectron Spectroscopy.

In contrast to PE techniques, contact potential difference measurement techniques produce a measurement of the work function of a sample relative to that of a probe tip, rather than producing an absolute value. An example device for performing a contact potential difference measurement technique is a Kelvin probe.

A Kelvin probe (KP) can measure a relative work function to a good degree of accuracy, for example 0.001-0.003 eV, but it is an indirect technique in that it does not measure the electrons directly (rather the flow of electrons in an electric circuit connecting tip and sample). In order to calculate the actual work function of a sample, the vibrating electrode (tip) needs to be calibrated against a known standard, or alternatively a photoelectric work function measurement needs to be performed on the either the tip or a reference sample.

The photo-electrons (which may have originated at different depths in the sample interior) can leave (or are ejected from) the material if they can overcome the surface work function. Any conditions which infer a low work function (sample composition variations, surface geometry or structure, contamination, etc) will enhance the photo-electron yield. Ejected electrons can then collide with air/gas molecules and drift towards the tip (which can be held at a positive voltage), producing a tip electronic current, which can be converted to a voltage and amplified.

FIG. 10 shows a dual mode detection system, comprising a photoemission measurement apparatus and a contact potential measurement apparatus. The dual mode system may comprise a probe tip and a sample that are in a gaseous environment, or in a vacuum. The right hand side of the figure shows a probe tip 502 functioning as a contact potential measurement probe, such as a Kelvin probe. The probe tip 502 is provided as part of or coupled to a contact potential measurement system 504.

The left hand side of the figure shows the same probe tip 502, functioning as a detector electrode for a photoemission detection technique. The probe tip 502 in that mode is provided as part of or coupled to a photoemission measurement system 508. An optical element 510 may also be provided to focus radiation from a light source onto a target area 512 on the surface of a sample 514. An example form of radiation is ultraviolet (UV) light. The optical element 510 and/or light source may form part of or be incorporated within the measurement system 508.

The purpose of the figure is to illustrate the different modes rather than the physical structure—so, while there are two separate representations of the probe tip 502, those do not represent different tips but in fact represent the same tip in different operation modes. The tip and detection circuit does not change as between the different modes, but the analysis routine does as the sample and tip voltages change, and as the nature of the illumination changes.

For the purposes of illustration, the sample 514 may comprise a layer 516 of Gold (circa 30 nm thick) on top of an Aluminium substrate 518 is shown. These example materials and dimensions are in no way limiting on the scope of the invention, they serve to illustrate one possible example application from many possible examples.

In the photoemission mode, a UV beam of light is focused on a spot 512 on the sample 514 and the UV photons of light have sufficient energy to create photo-electrons in the bulk of the sample 514, which, if their energy is sufficient to overcome the surface work function, will exit the surface, collide and stick to air/gas molecules (usually within about 3 microns or so from the surface), and be collected as an electronic current by the non-vibrating tip 502. The spatial resolution is governed by the size of the optical spot on the sample, as the area illuminated by the focused "spot" is the only region where photoemission occurs. The spot size may be a number of millimeters in diameter, but could be smaller and may be as low as 1 micron. The depth resolution will depend upon sample type and energy of the incoming photons.

The photoemission process will occur under ambient conditions, controlled ambient gas (such as $N_2$), variable relative humidity (RH) and also in vacuum. In the case of a sufficiently low vacuum then the emitted electrons can travel directly to the tip, although (as in air/gas) they are subject to any electrical fields between the tip and sample.

In the CPD measurement mode, the tip 502 vibrates, which modulates the capacitance of the tip-sample arrangement. In this technique the tip can be vibrated with a relatively large amplitude of oscillation (up to 2 mm) using a low-voltage voice coil type driving element located in a shielded housing some distance (for example, 100 mm) from the tip. In the direction of the electrical fields lines 522 indicated it is assumed that the tip and sample are in electrical contact and the work function of the tip 502 is less than that of the upper layer 516 of the sample 514.

The data may be processed as follows: A set of two or more (Vptp,Vb) data are recorded, producing a straight line as Vptp is proportional to the difference in average work function of the tip and sample work functions. The intersection point with the Vb axis is determined, which provides Vcpd; and the gradient is calculated which provides information on the fractional change in capacitance (proportional to $d_0^{-1/2}$ where $d_0$ is the mean spacing.

The $V_{cpd}$ data may be accurate to 1-3 mV and the gradient data is useful in two ways: when the probe is retracted and the sample changed then the probe tip can be accurately repositioned to exactly the sample spacing to sub micron resolution. In this fashion, the effects of parasitic capacitance, which can be already reduced by design, is held constant. Secondly the gradient data can be used as a digital feedback signal to either the dc-component of the voice coil driver or the z-axis of the probe position to maintain spacing during linescans or work function topographies.

Note the system utilises the Vptp signal (sum of all frequencies) rather than either the first ($\omega_1$) or second ($\omega_2$) fourier series components as, for high modulation indexes, the magnitude of Vptp can be 5-20 times greater that individual fourier components produced by lock-in-amplifier systems.

Null based system are prone to error, because the detection system adjusts the dc-potential of one of the plates so that a field free zone exists between the two plates (tip and sample). However the driver system requires energy and in piezoelectric driver systems this involves a relatively high driving voltage (typically 10-300 V) on surfaces which are typically a few mm away from the detection circuit. "cross-talk" of this driving voltage would confuse the detection system, i.e. the dc-feedback potential is trying to balance the true Vcpd and the erroneous the drive cross-talk (noise), rendering the output unstable.

In the current arrangement it is feasible to switch between the PE detection mode and the CPD detection mode, for example by simply using a shutter on the UV light source. The dc-potentials of both tip and sample (Vtip, Vsample) are connected to separate digital-to-analogue converters (DACs) which are automatically controlled by a measurement algorithm. As the PE signal and the CPD signal are derived from two independent frequencies, namely those of the optical shutter and voice coil driver, then it is possible to measure both data sets either simultaneously or independently.

In the figures sketched here some latitude has been taken with the orientation of the Kelvin probe-sample arrangement, the angle of illumination and the angle of the tip with respect to the sample normal. In traditional (vibrating tip) Kelvin probe mode the ideal arrangement is that the tip vibrates plane parallel to the surface, however the method still works well if the vibration is off-parallel, say at 45 degrees to the sample surface, or indeed any angle so long as the motion of the tip has a component that is normal to the sample surface, such that the separation changes. The separation distance also depends upon the tip 502 diameter and the amplitude of oscillation, but as a general guideline for a generally plane parallel arrangement it will be half the tip diameter, assuming the sample area is much bigger than the tip.

In KP-APS mode the spacing between the tip 502 and sample 514 is not very critical, however it is important that the contact potential difference (CPD) between the sample and the tip is known so as to correct for the resulting electric-field in KP-APS measurements. Due to parasitic capacitance effects the measured CPD is spacing dependent.

In KP-APS the angle of light injection will affect the penetration depth of photons in the sample and thus the information depth of exiting photoelectrons, and so depth-dependent information (for example, studying coating thickness in PE mode) can be extracted by controlling the angle of light injection.

The orientation of the sample and tip in the horizontal and vertical plane is not critical as the gravitational force acting on an electron in the downwards direction is approximately $8.94 \times 10^{-30}$ N and for a negatively charged oxygen molecule is $5.26 \times 10^{-25}$N. However, as an illustrative example, the force on a negative charge electron or air molecule due to a potential difference of +10 volts between tip and sample separated by 3 mm is $5.4 \times 10^{-15}$N. Thus the electric field interaction dominates greatly (i.e., $10^{10}$) over the gravitational interaction and even if the spacing is changed or the (positive) voltage decreased then it is still the dominant selector of the drift of charge carriers in the intervening space. The accuracy of the measurements may also be degraded if external air currents are present or if the sample is sufficiently heated such that air convection currents play a role. In general, the sample environmental enclosure should be controlled to avoid external air currents. Thermal convection currents can be mitigated by mounting the sample 514 in a horizontal plane underneath the Kelvin probe tip 502.

Ultra-violet Photo-electric Emission Spectroscopy (UPS) occurring in a (high or ultra-high) vacuum where the ejected electrons have a high mean-free path is a well-known technique and the Ultraviolet light source is typically a Helium (He) source of energy range 21.2-40.8 eV, significantly higher than range of material (metal) work functions of say 2-6 eV. The high photon energy can modify thin layers and may result in surface charging or damage. Further the Helium discharge source may produce gaseous products that can contaminate or otherwise change the work function of the sample. The sample is required to be compatible with (ultra high) vacuum conditions. With modern semiconductor technology using very thin organic (polymer) films this is indeed a problem. UPS is not typically used to generate high resolution surface work function information, accuracy can be as low as (0.25-2.00) eV. It is normally not used to form spatially resolved surface work function maps and UPS will not work in air, nor is it fast.

The Kelvin probe Air Photoemission System (KP-APS) as shown in FIG. 10 can operate under ambient (atmospheric pressure) conditions—(air, controlled gas, relative humidity and vacuum). An advantage of this system is that it can work in "dual" modes—as a Kelvin probe for high accuracy relative work function measurements and, using a ultra-violet light beam incident on the sample, as an absolute work function probe. It is possible to take simultaneous measurements of the two modes, or to perform each measurement mode sequentially (in either order, and on the same or different parts of a sample). All methods can be performed while scanning the sample spatially. Simultaneous measurement using both modes is described in FIG. 18 where the different signals are selected by frequency.

As the mean-free-path of electrons in air is rather small (a few microns) one would not expect photo-ejected electrons to be able to be collected by a tip located relatively far away from the sample surface, say at a distance of 0.5-3 mm. However this is not the case and electrons or electrons attached to (otherwise uncharged) gas molecules in the air can move from the sample surface to the Kelvin probe tip giving a detectable current, provided the photons in the light beam have sufficient energy to liberate the electrons in the first place.

Operation (in the KP-APS modes of varying the photon energy at constant tip potential and varying the tip potential at constant photon energy) has been verified in several ways: the sign of the detected current agrees with that of electrons or negatively charge gas molecules. Further, the magnitude of the measured current agrees with that expected by theory, that is the square root of the detected current plotted against photon energy will be linear for conductors (metals) and the cube root for semiconductors. Lastly the photo-electric work function (determined as the intersection of the processed detected current to the zero level (or noise level)), agrees with literature data.

The various components that make up the system of FIG. 10 will now be discussed.

The light source used will typically be an Ultra-violet (UV) broad-band source such as a Deuterium (D2) Lamp that can output UV photons of wavelength from 160-400 nm, corresponding to photon energies of 7.75-3.1 eV. It is also possible to use alternative discrete light sources such as UV Light Emitting Diodes (LED's) or UV Diode Lasers, which are also capable of causing photoemission.

Light in the visible spectrum has lower energy than that in the UV spectrum, so it will only liberate electrons from materials having a low work function, such as alkali metals, e.g. Cs, Na, K or low work function metals such as Gd. A Quartz Tungsten Halogen (QTH) source sources of wavelength 350-1200 nm corresponding to photon energies of 3.5-1.0 eV, i.e., visible and Infra-red, is a suitable light source in this regard.

In the following it will be assumed, unless otherwise stated that 'light' represents UV wavelengths. Further, the 'white light maximum' corresponds to transmission of all wavelengths from the source. In general the light source will be housed within an enclosure that is filled with Nitrogen gas to prevent to formation of ozone (O3) due to the action of UV light on oxygen in air. Further, all the components of the optical system (which may comprise some or all of the light source, wavelength selector, chopper, shutter, $N_2$ atmosphere and focusing), together with Kelvin probe parameters (which may comprise some or all of amplitude of vibration, mean tip-to-sample spacing, tip potential, sample potential, sample holder potential, sample (x,y,z) position, sample temperature, sample relative humidity, sample ambient) are capable of automatic control.

The light emitting from the D2 lamp can pass through a wavelength (or energy) selector. This can for example take the form of a diffraction grating, prism, linear filter, or discrete (interference) filter. In general the choice of the energy selector will define the transmission intensity and distribution of wavelengths, corresponding to a Full-Width at Half-Maximum (FWHM) of say 5-20 nm depending upon the optical arrangement utilised.

The light can also pass through an optional optical chopper which will produce a modulated light output at the frequency of the chopper wheel. An optical shutter can optionally provide low frequency light beam modulation.

The light from the optical system can be either focused directly onto the sample surface to be examined, for instance through a set of optical lenses specially selected to transmit UV light, or it can instead be coupled into an UV optical fibre which then transmits the light from an enclosure housing the light source to that housing the sample. Utilisation of the UV optical fibre may reduce the maximum energy of photons incident on the sample.

FIG. 11A shows a broad band UV light source 600 such as a Deuterium Lamp focused into a monochromator type wavelength selector 602. The full-width-half-maximum of the monochromator is typically 5-20 nm and this wavelength may be automatically controlled by a stepper motor and associated controller (not shown). The selected wavelength is optionally passed through an optical chopper 604 and then focused into a flexible UV optical fibre 606. The fibre 606 can then transmit the light into a measurement enclosure that may take the form(s) of a dark enclosure, a relative humidity enclosure, a controlled gas enclosure or a vacuum chamber, for example.

In FIG. 11A the components are housed in an enclosure 608 which can be filled with air or alternatively a gas, such as Nitrogen. Using a Nitrogen atmosphere prevents the formation of Ozone and associated adsorption of UV light.

The objective of the chopper 604 is to produce a modulated UV light output, having frequency $\omega_{PE}$. If the chopper 604 is not used then constant light intensity, so-called DC light, results. An optical shutter (not shown) located between the chopper 604 and the final optical focusing assembly 'C' allows the beam to be switched on and off automatically or selectively.

FIG. 11B shows a similar arrangement, in which like components are illustrated with like reference numerals. However here a sample 610 is housed within the light enclosure 608 (and sharing the Nitrogen atmosphere). In this case (and other similar cases) the recorded intensity of high energy photons is increased because any unwanted absorption as would occur in the optical fibre of FIG. 11A or by air in the atmosphere is reduced.

A further variation is possible, shown in FIG. 11C, whereby the sample atmosphere is controlled independently of the atmosphere required or used for the light source. An appropriate window could be provided at a terminating portion of the enclosure for the transmission of light.

Another optical configuration would be a broad-band light source, which passes through one or more interference filters. The interference filters would select a fixed wavelength and may be mounted on a linear or rotational holder which may be capable of automatic or selective manipulation.

FIG. 12 shows a broad band light source 700, which may be a UV light source such as a Deuterium Lamp focused into a filter type wavelength selector 702. The full-width-half-maximum of the filter 702 is typically 10-20 nm and the filter 702 will transmit between approximately 20% and 90% of the incident light at its design wavelength. The filter 702 can take the form of a number of interference filters (see FIGS. 13A, 13B) which can be rotated into place to provide wavelength selection. Alternatively the filter may have a linear geometry (see FIG. 14) either discrete or variable (continuous), where the linear output wavelength is elected by translational position. In both rotational and translational mechanisms it is useful to keep one slot open to allow direct passage of the high intensity 'white light' spectra. The light is then optionally passed through an optical chopper 704. The light source enclosure 708 may be filled with a $N_2$ atmosphere.

In the embodiment of FIG. 12A the light is conveyed to a sample 710 enclosure using a flexible UV optical fibre 712.

FIG. 12B shows a similar arrangement to that of FIG. 12A, in which like components are illustrated with like reference numerals. However in FIG. 12B the sample 710 is located within the enclosure 708.

A further variation is possible, shown in FIG. 12C, whereby the sample atmosphere is controlled independently of the atmosphere required or used for the light source. An appropriate window could be provided at a terminating portion of the enclosure for the transmission of light.

FIG. 13 shows examples of discrete rotational interference filters, of the type that may be used in the example embodiments shown in FIGS. 12A and 12B. In FIG. 13A, wavelength selection is performed by rotating a discrete interference filter 800 in the path of the UV light output from the source. Different filter designs may be used, but in the example of FIG. 13A, a twelve slot rotational filter is provided. It rotates with a rotational speed $\omega_A$. FIG. 13B shows an alternative embodiment filter 802 in which a reduced number of filters (here, four) is applied. The number of filters may advantageously be between two and four, which range is particularly suited to the high speed off null photo-electric threshold approach mentioned above. In this case the limited filter set may be rotated at speed $\omega_B$ (where $\omega_B > \omega_A$) permitting high speed photo-current measurements. It is possible to provide two filter wheels. A larger filter wheel, such as that of FIG. 13A for example can function to provide a selection of one from a set of different filters while a smaller wheel, such as that of FIG. 13B for example, could rotate continuously while data is recorded at high speed.

FIGS. 14 and 15 show alternative types of filters that can be used. FIG. 14A shows a fourteen slot linear discrete filter 900, including a white light maximum position 902, while FIG. 14B shows a continuous filter 904, also including a white light maximum position 906. FIG. 15 shows an example of a visible 400-700 nm linear variable filter (LVF) 1000 with white light position 1002.

If the source is composed of UV Led(s) then the light intensity and the modulation frequency of each LED can be controlled using a suitably biased voltage waveform. The optical modulation frequency can range from DC (i.e. no modulation, or a modulation of zero Hz) to several kHz. If 2-4 LEDs are used quasi-simultaneously, for instance at different modulation frequencies ($\omega_{L1}$, $\omega_{L2}$, $\omega_{L3}$, $\omega_{L4}$) then the contribution at each wavelength (energy) to the total detected current can be measured and the electron yield and the photoelectric threshold calculated in real-time.

FIG. 16 shows a multiple UV LED source (each source labelled as LED1-LED4), where each source is capable of individual automatic or selective control of intensity, phase and modulation frequency ($\omega_{L1}$, $\omega_{L2}$, $\omega_{L3}$, $\omega_{L4}$). The light output from each UV LED is transmitted via UV optics 1100, 1102, 1104, 1106 to the sample 1108 and any photoelectrons are detected by the tip 1110. In the case that all LEDS are used simultaneously then the total detected current will be the sum of each contribution. If the total detected current is de-convoluted by frequency (in a similar fashion to the KP, PE and surface photo-voltage (SPV) information depicted in FIG. 18 below) then the photo-electron intensity of each energy can be determined and the linear plot of the square-root of the intensity versus energy results in the determination of the photoelectric threshold or work function of the sample.

Referring now in general to the various aspects and embodiments of the present disclosure, if a small UV fibre is used, for example 100 μm-3 mm in diameter, then it can be mounted so as to illuminate an area underneath the Kelvin probe tip located directly above (in the orientations as illustrated) the sample surface. The Kelvin probe tip may be connected to a high-gain amplifier and voice-coil actuated suspension system. The tip potential may be automatically steered in a voltage range, for example −10 to 10 Volts. The light output from the fibre can be focused, increasing the light intensity underneath the sample, the associated ejection of photo-generated electrons, and the spatial resolution.

In the photo-emission case the spatial resolution may range from 1 micron to 10 mm. The profile of the spot will depend upon the angle of illumination relative to the sample surface. The illumination angle also has the effect of changing the depth of at which UV light penetrates the sample and thus the depth at which photoelectrons will be generated inside the sample.

FIG. 17 illustrates an additional implementation option wherein the a dual light source is provided comprising a UV source and a visible and/or Infra-red source. This arrangement is an "energy selective" device.

UV light will create photoemission if the photon energy is equal to or greater than the work function of the surface. If the sample is semiconducting then illumination of the sample can result in the semiconductor developing a surface potential that is dependent upon the intensity and energy of the photons. If single-frequency, or white light, is used then this is termed the Surface Photovoltage (SPV). If the frequency of light is varied then the technique is termed Surface Photovoltage Spectroscopy (SPS).

The characteristics of the Photovoltage spectrometer are similar to that already described for Photoemission, however typically the light source spectrum is in the visible and Infrared regions. SPV and SPS have both constant intensity (DC) and modulated intensity (AC) detection modes. In DC mode the Kelvin probe vibrates and it records the change in surface potential directly. In AC mode the Kelvin probe does not vibrate and the peak-to-peak output signal is recorded. In both modes the signal can be recorded as a function of incoming photon energy. The DC and AC modes may produce difference information depending upon the light induced carrier mobility within the semiconductor.

FIG. 17A shows a UV Optical system based upon a Deuterium (D2) source 1200 capable of producing DC or variable frequency ($\omega_{PE}$), energy-selectable light between 7.75 and 3.1 eV and transmitting this beam towards the sample source at a angle determined by the UV fibre mounting mechanism. This equipment, together with a suitable controlled Kelvin probe detection system can be used to determine at high speed, the photoelectric work function, the electron yield and the density of states of the sample under study. If the sample is positioned (scanned) underneath the light beam, then these parameters can be mapped with the spatial resolution of the light spot.

FIG. 17B shows a visible-infra-red source 1202 based upon a Quartz-Tungsten-Halogen (QTH) source capable of producing light of energy 3.5-1.0 eV, DC or variable frequency ($\omega_{SPV}$), which is conveyed to the sample using a visible/infra-red fibre For semiconductor surfaces (or coatings) and semiconductor devices, such as solar cells, this equipment, together with a suitable controlled Kelvin probe detection system can be used to determine at high speed, the semiconductor surface potential (SP), the semiconductor surface-photovoltage (SPV), the semiconductor surface photovoltage spectroscopy (SPS), semiconductor band-bending and for a solar cell the change the open circuit photo-voltage If the sample is positioned (scanned) underneath the vibrating tip these parameters can be mapped out with the spatial resolution of the tip diameter.

If the optical chopping frequency of the UV light source ($\omega_{PE}$) is selected to be different to that of the Surface Photovoltage light source ($\omega_{SPV}$) then the two measurements can be conducted in a simultaneous or quasi-simultaneous fashion.

FIG. 18 shows a frequency/output signal amplitude plot summarising the detection modes of a Kelvin probe system equipped with a combined UV and Visible/IR light injection system. The DC components comprise Kelvin probe DC SPV/SPS and DC PE measurements. The Kelvin probe CPD measurement is performed at $\omega_{KP}$, the AC-SPV/SPS measurement at $\omega_{SPV}$ or $\omega_{SPS}$ and photoemission measurements at $\omega_{PE}$. The respective vibration and chopping frequencies are use-selectable, so they can be kept sufficiently separate so as to be easily separated by suitable digital or analogue filtering. In principle the system is capable of all modes in a quasi-simultaneous fashion. This combined system can be used for measurements in air/gas. An advantage of such a system is than it can relate changes in sample (surface) work function and surface potential to material composition and performance occurring in the nm-μm region underneath the surface.

Now, the PE measurement techniques mentioned above will measure the photoelectric threshold (or photoelectric work function or fermi-level) of a metal or metal coated sample and the valence band maxima (VBM) of a semiconductor sample. Photoemission methods cannot measure the work function of a semiconductor directly as there are no free electrons in the semiconductor at the fermi level, $E_f$.

For semiconductors in air the VBM represents three energy steps ($eV_d + e\chi_s + E_g$ as represented in the summary diagram of FIG. 31, which includes information about PE as well as other processes not being discussed in this paragraph) corresponding (respectively) to the energy across the outer oxide layer, the energy related to the electron affinity and the bandgap energy. However the semiconductor work function, $e\phi_s$, under dark conditions is composed of the first two aforementioned elements plus the energy related to the semiconductor surface potential and the energy difference between the conduction band and the fermi-level, i.e. $eV_d + e\phi_s + eV_S + eV_n$.

If now the semiconductor is illuminated solely by a "white" light source (either directly or via an energy selective device such as that of FIG. 17B) then a CPD analysis of the change in semiconductor work function with low light intensity illumination will yield the semiconductor surface potential $eV_S$. Adsorption of photons across the semiconductor bandgap produces mobile holes and electrons. If the semiconductor surface is negatively charged then positive holes will be attracted, tending to temporarily nullify the surface charge. Consequently the semiconductor energy bands flatten and the surface potential diminishes to zero. In summary the CPD change, i.e. CPD (illumination by $\geq E_g$ photons)-CPD (Dark) produces the semiconductor surface potential. This is termed a surface photo-voltage measurement Vspv.

If the above measurement is repeated using now a variable photon-energy light source, such as that of FIG. 17B, then the photon energy at which Vspv is first detected equates to the semiconductor energy gap $E_g$. In this analysis it is assumed that there are no surface states within the semiconductor band-gap. If this is not the case (as shown for example in FIG. 32) then the resulting photon-energy spectra, termed surface photo-voltage spectroscopy (SPS), will contain information both on the semiconductor band gap and surface states in the oxide layer.

So in summary the PE measurements can provide various measurement modes including:
1. Photoelectric threshold of a semiconductor. Using air (or other gaseous environment) photoemission measurements the energy difference between the valence band maxima (VBM) and the Vacuum Energy (Evac) can be established.
2. Photoelectric Work Function for metals.
3. Photoemission spectroscopy or density of states for metals and semiconductors.

The CPD measurements can provide various measurement modes including:
A. CPD (Dark)
The work function difference between the metallic vibrating tip and the sample (semiconductor or metal) work function
B. CPD (Illuminated)-CPD (Dark), for semiconductors:
1. Change in Surface Potential of the Semiconductor.
2. Energy Gap of the Semiconductor.
3. Spectrum of Surface States.

One example application of the above methods is to measure a semiconductor PN junction, which may be useful for testing various products such as solar cells. If a semiconductor sample takes the form of a PN junction or solar cell then the CPD measurements allow the open circuit voltage Voc of the cell to be determined. In the ideal case Voc represents the difference in fermi-levels between the n and p regions making up the junction.

Sometimes a semiconductor device will comprise multiple PN junctions, which is the case for example in modern organic photovoltage (OPV) solar cells. Examination of the surface photo-voltage spectrum measured using CPD techniques allows information to be gained about the electrical behaviour of the solar cell under illumination corresponding to the light spectrum emitted by the sun. This is termed surface photo-voltage spectroscopy (SPS). The accuracy of SPS may be enhanced by chopping the light source and measuring the resulting Vptp rather than vibrating the tip electrode.

Another component of the system is the holder or enclosure for the sample.

The sample may be housed in an enclosure that serves the function of a Faraday cage, i.e. minimises the intrusion of external electrical and magnetic fields. The sample enclosure may be capable of being light-tight, and may have air or a controlled gas such as nitrogen as an ambient. The enclosure may have a dimension such that its walls are far enough away from the sample to avoid reflecting radiation back onto the sample. The walls may also be darkened to help reduce spurious reflections. The relative humidity of the air may be controlled and optionally the chamber may be evacuated, see FIG. 17 RHS. The sample may be mounted on a variable temperature heater stage. In general the sample temperature and environmental conditions will affect (modify) the sample work function.

The sample may be mounted on a metallic sample plate or stage that is capable of being automatically biased electrically with respect to ground, for example −70 to +10 Volts (DC). The sample mounting plate may reside on an automatic (x,y,z) scanning platform.

The sample can be scanned to provide either a CPD topography or a Photoemission threshold topography. The sample to tip separation ($d_0$ as illustrated in FIG. 30) in CPD mode can be controlled using the gradient of the Vptp versus Vtip data set. Typically a modulation index is the range 0.5-0.8 is required for optimum CPD measurements. Photoemission measurements are not very dependent upon the z-separation of the tip and the sample and the tip can be at the same position as for CPD or even further away, say 1-4 mm as required. Both sample and tip potentials may be connected to independent digital to analogue converters, whose programmed operation depends upon the (selected) measurement mode.

The sample may be fastened on the sample table, for example using metallic spring clips or Aluminium tape with conducting glue. The function of the securing mechanism is to mechanically hold the sample in place and make an intimate electrical contact with the sample top surface, or a conducting layer near the sample surface. In the case of a conducting samples such as metals or semiconductor wafers, firm mechanical contact with the sample mounting plate may be adequate for electrical contact. In general the sample mounting mechanism will be low profile and will ideally be located around the sample periphery in such a fashion that it will not influence any measurements.

Samples will consist of (bulk) metals, metal alloys, semiconductors, insulators, liquids, polymers, or composites. An insulating, semiconductor or conducting substrate may be covered with one or multiple layers which may also be insulating, (semi)-conducting. Samples may also comprise conducting polymers or biological tissue. In the case of powder or liquid samples, the sample can be held in an appropriate container below the tip. A sample heater/cooling stage can be placed underneath the sample, for example using resistive-heating or cooling/heating using a peltier junction.

Samples may be clean or contaminated (either intentionally or otherwise). Physical debris on the sample surface such as particulate matter should be avoided unless the sample is itself a powder. The sample may be a liquid surface with or without a thin film.

It will be appreciated that the sample holder and the sample may comprise multiple ones of the various optional characteristics and properties of as mentioned above may exist together. Because a wide variety of options have been mentioned, it is impractical to list the various ways in which the features may be combined. However it will be apparent to a person skilled in the art which options are mutually exclusive from a technical perspective and the present disclosure is not intended to encompass any such mutually exclusive combinations of features.

A similar detector is used in the various aspects and embodiments mentioned above, and the design of the detector will now be discussed.

The detector in a preferred embodiment comprises a flat metallic tip suspended above the surface to be studied. Such a detector is termed a Kelvin probe. The tip may be either vibrating or held stationary. The tip size can vary, although a preferred range is from 5 microns to 20 mm in diameter (different tip sizes may be selected for different sample sizes—typical samples may have a characteristic diameter of between a few mm to 350 mm, although the invention is of course not limited to this range of sizes). The tip diameter defines the spatial resolution in CPD measurements. The tip may have a circular geometry and this may have a section or sections removed to enhance by reflection the amount of light incident on the sample surface. The tip may be semi-transparent to the illumination beam. Alternatively the tip can be fabricated from a high or low work function material such as Platinum (Pt), 5.65 eV or Aluminium circa 4.0 eV. The tip can also be coated with a thin layer of another material.

The metallic tip (which may comprise an integral pre-amplifier stage) is mounted on an automatic stage that can position the tip directly above the sample surface. Using existing equipment, the tip to sample spacing can be adjusted in increments of 317 nm. The metallic electrode may be connected to a current pre-amplifier (operational amplifier in a current-to-voltage configuration). The effective pre-amplifier gain will be between 10E6 and 10E10 depending upon the magnitude of the feedback resistor. The direct connection of the vibrating tip to the input pin of the amplifier makes the time-varying Kelvin signal much less susceptible to external noise.

The tip signal can be processed with one or more further voltage sensitive amplifiers with a gain of between 30 and 3000. The voltage amplifiers may include low or high pass filtering such that a discrete signal at the mechanical vibration frequency of the Kelvin probe or the chopper frequency of the illumination UV light system can be separated. Noise reduction can be performed as boxcar integration using a reference signal of either the probe spacing modulator or the optical light modulator.

The overall gain of the electronic system varies from 3E7 and 3E13, this takes into account different tip diameters, tip geometry, sample geometry, sample structure and sample temperature, tip to sample spacing, sample electrical characteristics, environmental characteristics (air, controlled gas, relative humidity, vacuum) and integration of other techniques requiring space around the sample. The voltage of the tip is automatically adjustable (to milli-volt resolution) between +10 and −10 Volts.

The tip/amp may be located on a voice-coil driver with a resonance frequency between 50-300 Hz. The amplitude of tip oscillation can be adjusted with micron resolution between 0-5000 microns (peak-to-peak) using a sinusoidal AC waveform applied to a voice-coil displacement system (driver). The suspension system is comprised of two or more stainless-steel diaphragm springs. In the case of a vacuum implementation the tip amplifier is located on the atmospheric side of a vacuum feedthrough.

FIG. 19 illustrates the gains applied for air photoelectric emission. A constant (DC) or modulated (AC) intensity UV light beam 1600 is incident upon a conducting sample 1602. If the photon energy (Eph=hf, where 'h' is Planck's constant and 'f' is the frequency of light) is equal to or greater than the photoelectric work function of the sample 1602 then photo-electrons will be ejected and can cross the space between the sample surface and the (non-vibrating) Kelvin probe tip 1604. The electron current registered at the tip 1604 will be increased if the tip 1604 is held at a positive voltage with respect to ground potential (Vtip) and if the sample 1602 is held at a negative potential (Vs) with respect to ground potential. The electrons collected by the tip 1604 pass through a current-to-voltage converter 1606 with Gain A and a voltage amplifier 1608 with Gain B, where the total gain A*B is in the range 3E7 to 3E13. For example an initial 5 fA negative-ion current would be converted to 100 mV signal at the amplifier output. This negative-ion detection system can accommodate input signal of under 1 fA to above 100 nA, corresponding to negative ion streams ranging from $6.25 \times 10^3$-$6.25 \times 10^{11}$ counts per second. These high count rates are a distinct advantage if the sample surface exhibits poor electronic emission characteristics or is a semiconductor. A data acquisition system (DAS) averages, performs noise reduction, processes and records the signal in real-time.

Signal processing, to increase the signal-to-noise ratio, can be performed in the following ways:
1. By performing a number of sequential, asynchronous measurements, say 200 at a relative high acquisition rate of 10 kHz. This procedure is repeated say 50 times and the voltage data is summed and averaged. The total acquisition time in that scenario is 0.1 seconds.
2. Synchronous measurements using a period trigger signal provided by an optical chopper which is inserted to the primary light beam. The data acquisition system repeatedly measures the signal change (or peak to peak) due to a illumination-dark transition. This can be averaged 100-500 times in 1 second. The use of synchronous detection or 'box-car' detection will provide an enhanced resolution of the photoelectric threshold as it has an superior signal-to-noise ratio compared with non-synchronous detection, essentially because of the box-car nature of signal averaging and because it is in effect a differential measurement rather than an absolute one.

In both measurement modes the accuracy would be $10^{-5}$ of a volt, corresponding to initial negative ion currents <<0.001 fA.

FIG. 20 shows approximately two periods of an output signal for a vibrating Kelvin probe which is suspended just above a sample that is being illuminated with a DC UV light beam such that $E_{ph} > e\phi_S$, the KP tip being held at a positive potential(s). The peak to peak output voltage can be used to calculate the CPD and thus the KP work function (assuming suitable tip calibration) and two or more measurements of the DC offset (at different positive tip potentials) can be used to determine the gradient of the electron yield and thus the photoelectric work function. These work functions will diverge if the material is inhomogeneous in depth, so this combined system can be used to probe for inhomogeneities in a surface coating.

Aspects of signal processing for various modes of operation of the system will now be described.

EXAMPLE MODE 1

Kelvin Probe Processing—Sample Dark, Vibrating Tip

Here the Kelvin probe (KP) is vibrated and suspended a short distance above a conducting surface. The voltage on the tip or sample is automatically controlled. Two or more set voltages generate two or more peak-to-peak output signal heights. This data can be used to determine changes in mean spacing to sub-micron resolution and independently the contact potential difference (CPD) between vibrating electrode and the sample to within 0.001-0.003 Volts. The CPD is generated by the average work function difference across the tip and sample surfaces. The CPD measurement can be performed at high speed up to 30 Hertz.

The Kelvin probe enjoys a very high surface sensitivity—it is sensitive to very small changes in the sample surface occurring in the top 1-3 atomic layers. In the non-scanning case any sample work function changes can be recorded as a function of time due to process occurring in the top-most layers due to deposition, adsorption, surface roughness, etc. If the tip has first been calibrated against a reference surface of known work function then the CPD data can be adjusted to produce absolute work function values. Due to the effects of parasitic capacitance it is desirable that if two materials are to be compared with a Kelvin probe that the mean spacing is identical (within a few microns) and that all other system parameters remain constant.

If the tip is scanned across the surface the sample topography and the contact potential difference will be mapped with a spatial resolution of the tip diameter.

EXAMPLE MODE 2

Kelvin Probe Processing—Semiconductor Sample, Sample Illuminated, Vibrating Tip

If the sample is a semiconductor then changes of the surface potential of the semiconductor (due to light adsorption) can be studied. In this case the optical system can be used to inject light that stimulates charge carriers (electrons and holes) to make electronic transitions either at the surface of the semiconductor or in the bulk. In this case automatic control of the light intensity, optical shutter (to invoke a dark/light and light/dark transition) and light wavelength can produce detailed information on the electrical characteristics of the sample.

EXAMPLE MODE 3

Kelvin Probe Processing—Semiconductor Sample, Sample Illuminated, Non-Vibrating Tip In this case the Kelvin probe does not vibrate, however the peak-to-peak signal is caused by the interaction of AC light injection with the semiconductor material. Similar measurements are performed as in Example Mode 2 above. In this case the CPD between tip and sample is unknown however, in a relative sense, this method may be more sensitive to spectroscopic data.

EXAMPLE MODE 4

Photoemission Processing—Non-Vibrating Tip DC UV Source

Here the non-vibrating Kelvin probe is suspended above a sample surface and the photoemission (PE) current is recorded as a function of the incoming light energy. The tip potential can be adjusted between 0 and 10 volts, but is fixed during measurement. An extraction potential can be used to 'drift' photo ejected electrons across the air gap between tip and sample.

The data are processed to reduce noise and produce material data including the photoelectric (absolute) work function, the photoelectric yield and the confidence limit ($R^2$). For conducting materials the processing involves plotting the square root of the current data versus energy and for semiconductors the cube root.

It is likely that the PE data will contain information from a greater depth than that of KP alone so any differences between the CPD and PE work function data may provide information about the sub-surface layers. Photoemission is sensitive to the lowest work function on the surface and typically the tip work function is not involved.

This measurement mode can be performed at two or more photo energies (see FIG. 9), to give high speed work function information. It can be performed at a lower speed to give Density of States information via Photoelectron spectroscopy.

EXAMPLE MODE 5

Photoemission Processing—Non-Vibrating Tip AC Source

This mode is similar to the DC mode however the AC signal can be detected by boxcar integration providing high speed and high S/N ratio. This measurement mode can be performed at two or mode photon energies (see FIG. 9), to give high speed work function information. It can be performed at a lower speed to give Density of States information via Photoelectron spectroscopy. This mode offers an improved measurement of the detector offset using the signal phase information provided at high signal levels.

EXAMPLE MODE 6

Photoemission Processing—Non-Vibrating Tip AC or DC Source Tip Potential Scan This is performed at a fixed photon energy ($E_{ph} > e\phi_S$) or white light illumination. The tip potential is scanned and the DC or PTP signal (corresponding to (DC and AC UV illumination) provide information on the sample and tip work functions, and the sample and tip density of states.

Differences between the information generated in PE and CPD measurement comprise speed, absolute or indirect (relative) work function, work function resolution, spatial resolution, and information depth. In the PE technique the method is sensitive to the minimum work function of the illuminated area; in the KP/CPD mode the average work function underneath the vibrating tip. Both methods work in air on a range of sample types. It is likely that the KP/CPD method can be preferentially applied for samples displaying poor conductivity as it is relatively unaffected by high serial resistance.

It can be seen that the disclosure also provides new spectroscopic methods for measuring the surface density of states (DOS).

In a first DOS measurement method, the KP tip is held at a constant positive voltage and does not vibrate. The energy of the photons is scanned, the photoemission current is detected in either DC or AC mode (i.e. either an optical chopper is used or it is not used) and this gives the photoelectric threshold (work function) and for energies above the above the work function, the density of states information which is obtained by differentiating the (integral) current, where the integral current is the detected current at any energy. The plot is of similar form to the $I^{1/2}$ versus $E_{ph}$ graphs of FIGS. 8 and 9.

In a second DOS measurement method, the Photon energy is held constant at an energy resulting in photoemission. The tip is not vibrating. The Tip potential is scanned from, for example −10 to 10 V in 1-10 mV increments (in an example 200 steps may be used, but many more could also be used), the photoemission current is detected in either DC or AC mode (i.e. either an optical chopper is used or it is not used). In this new characteristic the plot is $I^{1/2}$ can then be plotted against the tip potential. The information generated includes the sample work function, the tip work function and the sample Density of states and the tip density of state. In each case the density of states information is obtained by differentiating the (integral) current, where the integral current is the detected current at any energy.

FIG. 21 shows a schematic of the overall control system comprising UV Spectrometer control for PE measurements, Visible, Infra-Red Spectrometer for SPV/SPS measurements, Data Acquisition system, signal processing control, Kelvin Probe Control parameters, Sample and Tip Positioning Control and Sample Enclosure control comprising environmental and sample/sample stage parameters. Not shown is an optical microscope system showing the tip to sample spacing and the position of the tip on the sample. All control sub-system interact with the main PC or microcontroller host system via USB, serial or other communications bus.

In summary therefore, the present disclosure provides many significant advantages.

- The Determination of Absolute Work Function by Photoemission Emission (PE) works in air, variable relative humidity (RH), under controlled gas or in vacuum.
- The APS works on high signal levels and relatively short data acquisition times. It is in essence much faster than current techniques that require a long integration time to acquire sufficient signal.
- Additionally the APS has a rapid data (work function) acquisition mode that is substantially quicker than that currently available, i.e., PE work function data can be generated within 10 seconds or less, compared with 5-10 minutes with current systems. The resulting PE work function average with time generates data of accuracy (0.010-0.020) V, substantially higher than the (0.050-0.100) V currently claimed.
- The rapid mode is characterised by an emission current IE measurement at two or more light energies such that the signal levels are high. The emission data are corrected for any detector offset and linearisation of lamp output to produce IEcorr. Then the square root of the emission current is taken. The straight line through the (IEcorr)½ versus ELight is calculated together with the gradient of the line which corresponds to the sample electron yield. The intersection of the straight line with the baseline, corresponding to zero current (or detector dark-offset) represents the photoelectric-threshold or work function. As we extrapolate from high (discrete) signals levels the accuracy is improved with respect. As the number of discrete point is limited to two or more the method is fast.
- The KP-APS works in either DC (constant light intensity) or AC mode (chopped light intensity at a higher frequency, $\omega_I$), in AC mode, an advantage is that the signal to noise ratio is high, due to the box-car integration technique. Further in the AC mode the system intelligently uses the phase information (generated at high signal levels) to reduce noise around the threshold, making the PE system more accurate.
- The APS provides, via Photoemission Spectroscopy (where the illumination energy is scanned between a start value and an end value in, for example 100-200 steps) data on the material's local Density of States, i.e. energy levels close to the fermi-level, using relatively low energy light radiation which is unlikely to disturb or otherwise modify the sample surface.
- The APS provides information on the photoelectron yield, we can generate the PE gradient defined as Δ(PE signal)½/ΔELight. The PE signal may be measured either in the DC or AC mode.
- The APS has a high spatial resolution—the spot size can be in the range 50 microns to 10 mm. Assuming the light remains focused underneath the tip then PE work function linescans or topographies can be generated by moving the sample underneath the tip. This offers a greater potential than current system which illuminate a large area of the sample and have no scanning capability.

The Air Photoemission system has a dual PE-Kelvin probe mode.

The KP-APS has several modes: Photoemission, Photoemission Spectroscopy, Kelvin probe CPD work function measurements, Kelvin probe Surface Potential measurement, Surface Photovoltage measurements and Surface Photovoltage Spectroscopy Measurements. Such measurement can be made quasi-simultaneously by chopping the light at frequency $\omega_{Light}$ and vibrating the tip at a different frequency $\omega_{Tip}$. These modes can be combined, in air.

The KP-APS is capable of either independent or quasi-simultaneous CPD and PE work function measurements.

Any difference between the work function generated by CPD and PE may be due to:

A. The composition of the materials, thin film or layer. The Kelvin probe is probably sensitive to the topmost 1-3 layers of atoms, however light injection can give information about 10-1000 layers.

For example in the case of a thin layer (30 nm) of a high work function material such as gold (5.1 eV) deposited on top of a low work function material such as Aluminium (circa 4.0 eV) then the CPD measurement will generate only information about the topmost gold atoms, however the PE absolute work function measurement will generate information about the composite film, e.g. producing an intermediate work function. Thus the PE data is work function, composition and thickness dependent. The dual measurement helps decode this information.

B. The sample surface profile—non-flat surfaces may exhibit higher radius of curvature and the associated high electric fields around any protrusions may lower the effective work function.

C. The KP measures the average work function underneath the tip. The PE measured the lowest work function of the area illuminated.

Assuming that no external voltage is applied to the sample or sample holder, i.e. they are grounded, then a Spectroscopy method can be applied where the tip potential is scanned for example from −10 to 10 volts and the PE current measured. The illumination can be either monochromatic energy or broadband. This method effectively explores the sample and tip density of states and work function of the surface of both tip and sample.

If the UV light is only focused onto the tip and the tip is made of high work function material such as Pt, or the tip is sufficient removed form the sample so that no photoemission from the sample occurs then the (absolute) Photoelectric work function of the tip can be determined using a combination of light injection (higher in energy than the tip work function) and tip electrostatic potential.

SUMMARY OF CHARACTERISTICS

KP Mode

| Measures | Average Contact Potential |
|---|---|
| CPD resolution | 0.001-0.003 V |
| Speed of measurement | typically 0.4 Hz to 30 Hz |
| Spatial resolution | 50 μm to 10 mm (effectively the tip diameter) |

-continued

| Measures | Average Contact Potential |
|---|---|
| Work Function Depth | 1-3 nm of a metal surface |
| Scanning Mode | from (100 × 100) μm per side to (100 × 100) cm |

SPV/SPS

| Illumination | Generates Surface Photovoltage Spectroscopy |
|---|---|
| Resolution (DC) | as CPD |
| Resolution (AC) | <1 μV resolution |
| Spatial Resolution | as CPD |
| Speed | as CPD |
| Work Function Depth | up to 5 μm |

PE Mode

| Measures | Minimum Absolute Work Function of the sample |
|---|---|
| Speed | <10 seconds |
| WF Resolution | 0.010-0.020 V |
| Work Function Depth | 1-1000 nm |

Further Discussion Regarding Terminology, Definitions and Preferred Embodiments

To further assist in the understanding of the invention, FIGS. 22-32 present additional explanations of the terms that are used.

FIG. 22 illustrates a clean metal work function. The electrons 2200 in the metal are represented by hatched lines. The photoelectric work function of the clean metal, $\phi_m$, is the minimum energy required to remove an electron from the highest filled level (termed the Fermi-level) within the metal to a position "just outside" the metal. Just outside is typically 30 nm, i.e. beyond the range of the mirror force acting on the electron, this is indicated by the $E_{vac}$ level. If the metal is exposed to a gaseous environment such as air (a gas comprising $O_2$, $N_2$ and $H_2O$), then the electron quickly stops but may charge up an air molecule, creating a negative ion.

In this case theory suggests that the photoelectric work function equals the fermi-level, and it is the metal fermi-level that is involved (as one electrode) in contact potential difference (CPD) measurements. Note that in the CPD measurement it is the average work function of a distributed surface, i.e. the opposing faces of each electrode, that is measured, not the minimum work function. The two measurements will only agree if the capacitor involved is ideal, i.e. parasitic capacitance is not present and the two surfaces involved in the $V_{cpd}$ measurement are completely homogeneous. Note further that the electron involved is a conduction electron and is typically located in the selvage, i.e. the surface region.

FIG. 23 illustrates photoemission for an ideal clean metal, with electrons 2300 in the metal represented by hatched lines. Incident UV light 2302 (either continuous wave or chopped at frequency $\omega_{pe}$) with photon energy $E_{ph} \geq \phi_m$, causes photoemission. If the UV photon is adsorbed within the metal surface then it can promote an electron to leave the metal. The metal is typically grounded or held at a constant potential, otherwise it would quickly become positively charged and further electrons would not leave the surface.

The electrons interact with molecules or air within the mean free path region, typically 3 producing negative ions 2304. These ions are free to drift towards the positively biased (metallic) tip, shown to the lower right of the figure. The electron energy direction is upwards, so being positively charged, the tip is sketched below the fermi-level of the metal. The tip voltage $V_{tip}$ is quite low, say 5-10 V and it may be controlled by a DAC which is part of the data acquisition system. Similarly, the ion current effect can be enhanced by negatively biasing the metal sample, again using a computer controlled DAC.

The tip output signal is amplified as described above. This system allows high signal levels and thus high speed, high accuracy measurements. Signal processing may include averaging, automatic adjustment for wavelength dependent variations in light intensity, background noise level; then the square root may be determined and the Pearson correlation coefficient, yield and photoelectric work function can be determined.

FIG. 24 illustrates energy levels for an ideal clean (dark) semiconductor. Electrons 2400 in the metal (left hand side) and 2402 in a semiconductor (right hand side) are represented by hatched lines as before. The semiconductor is assumed to be clean and to display zero surface charge. The semiconductor is characterised by two energy levels/bands termed the conduction band $E_C$ and Valance band $E_V$, where the top of the valance band is assumed to be filled with electrons. The energy of the band-gap between $E_C$ and $E_V$ is termed $E_g$. The semiconductor fermi-level $E_f$ is typically termed by doping levels and the energy difference between the conduction band and the fermi-level is given by $eV_n$, where 'e' represents the electronic charge and $V_n$ is a voltage determined by the doping levels (the subscript n refers to negative charge carriers).

As there are no mobile electrons at the fermi-level then photoemission cannot directly determine the semiconductor work function $\phi_{semi}$ directly, rather the photoelectron threshold for this surface is the sum of the $\phi_{semi}$ and the energy difference between the fermi-level and the valance band, i.e. $eV_p$.

The energy difference between the conduction band and the vacuum level is $e\chi_e$ where $\chi_e$ is termed the electron affinity, this is typically a non-changing material parameter.

The figure shows equality in the fermi-level of the metal and semiconductor. However, in general this is not the case, but has been used here to clearly illustrate changes in the semiconductor work function (see FIG. 4).

FIG. 25 illustrates an energy diagram for a semiconductor (dark) with an oxide coating and no net surface charge. Electrons 2500 in the metal (left hand side) and 2502 in a semiconductor (right hand side) are represented by hatched lines as before. In this figure the semiconductor has a thin oxide coating depicted by a wide gap dielectric. The effect of this is to increase the semiconductor work function by a contribution $eV_d$, where $eV_d$ represents the voltage across the oxide and as drawn, would be due to an elementary dipole (layer of charge) at the oxide surface.

The semiconductor work function has increased by an amount equal to $eV_d$ and the photoelectric threshold of the semiconductor has also increased. We observe that a contact potential difference $V_{cpd}$ exists across the metal-semiconductor arrangement, where $V_{cpd}=eV_d$.

There is no charge at the oxide-semiconductor interface, i.e. $Q_s=0$. The semiconductor electron affinity $\chi_e$ is also unchanged, the energy bands within the semiconductor remain flat and the band-gap $E_g$ is unaffected.

In this case the semiconductor work function $\phi_{semi}$ has increased to $(\phi_{semi}+eV_d)$, the photoemission threshold again equals $\phi_{semi}$ and $eV_p$. The change in contact potential $V_{cpd}=V_d$.

FIG. 26 illustrates a semiconductor (dark) with a charged oxide coating, and a surface charge $\leq 0$. Electrons 2600 in the metal (left hand side) and 2602 in a semiconductor (right hand side) are represented by hatched lines as before. This figure is a realistic representation of a semiconductor in air. In this case a negative charge exists within the oxide and this has the effect of inducing a positive charge in the surface region of the semiconductor. This means that charge carriers in the near surface region of the semiconductor are subject to an electric field in the so-called double layer. In the present case the effect of the positive charge in the semiconductor is to bend the energy bands downwards. As the position of the fermi-level in the bulk (far removed from the surface) is determined primarily by semiconductor doping then it remains unchanged.

The net effect is to reduce the fermi-level and thus the work function of the semiconductor by an amount equal to $eV_s$ where $V_s$ is termed the semiconductor surface potential. However the photoemission threshold, being subject to the position of the valence band maxima, is unchanged.

In summary charges in the oxide coating can be determined via CPD techniques which are sensitive to the semiconductor work function. However they cannot be determined using photoelectric threshold measurements if the energy of the valance band maxima remains unchanged.

FIG. 27 illustrates a semiconductor under illumination with $E_{ph} \geq E_g$. Electrons 2700 and 2702 in dark and illuminated cases respectively are illustrated with the hatched lines. This figure shows that, when illuminated by low intensity light of photon energy greater than that of the semiconductor band-gap energy, light adsorption within the semiconductor creates free carriers which tend to reduce or nullify the semiconductor charge. This results in a flat energy band diagram, thus the difference in CPD between the illuminated and non-illuminated cases produces the surface potential $V_s$, i.e. $\Delta V_{cpd}=eV_s$.

FIG. 28 illustrates CPD measurement of a non-illuminated semiconductor PN junction, (i) before contact; (ii) after contact; and (iii) at balance point. The semiconductor sample is represented by a PN junction with the n-type region facing the metal vibrating electrode (Kelvin probe). In FIG. 28(i) the fermi-level in the semiconductor $E_{fS}$ is continuous across the contact and is assumed lower than the fermi-level in the metal $\phi_m$. Upon electrical contact the two fermi-levels equalise. As electrons are conveyed to the metal it adopts a negative charge and likewise the semiconductor surface adopts a positive charge of equal magnitude. The resulting voltage between the two surfaces is termed the contact potential difference, $V_{cpd}$, the value of which an be ascertained using a controlled tip potential and a signal detection circuit described herein. An energy difference $eV_{bi}$ exists between the n and p type regions of the junction where $V_{bi}$ is termed the built-in potential.

FIG. 29 illustrates surface photo-voltage spectroscopy of an illuminated semiconductor PN junction, with $E_{ph} \geq E_g$. If the junction (solar cell) is now illuminated with greater than band-gap energy light then mobile electrons and holes are created predominately in the p-type bulk region as the n-type surface region is often very thin, for example <100 nm. The resulting charge flow tends to decrease the built-in potential and consequently the energy bands in the n and p regions are closer together. The shift in the semiconductor fermi-level is $eV_{oc}$ where $V_{oc}$ is termed the open circuit voltage and this is measured directly by the Kelvin probe. In the case of modern organic photo-voltage (OPV) solar cells then typically multiple pn junctions are involved. Examination of the surface photo-voltage spectrum measured using CPD techniques allows information to be gained about the electrical behaviour of the solar cell under illumination corresponding to the light spectrum emitted by the sun.

FIG. 30 shows a schematic of a measurement arrangement that may be used in the embodiments described above. Here, the arrangement comprises two independently computer controlled optical sources 3000, 3002 with chopper and shutters for PE and illuminated CPD measurements. The angle of injection of the light beams (θ) can be controlled, for example to study coating thickness in PE mode.

The sample 3004 is mounted on a x,y,z stage 3006 with the tip 3008 (collector) positioned above. The sample 3004 can be scanned to provide either a CPD topography or a photoemission threshold topography. The sample to tip separation ($d_0$) in CPD mode can be controlled using the gradient of the $V_{ptp}$ versus $V_{tip}$ data set.

The enclosure walls are at least a distance, x, away from the sample-tip arrangement and may be darkened to eliminate spurious reflections. The distance x may be chosen depending on the specific geometry of any particular sample and/or tip. However a wide range of samples can be analysed when the distance is 225 mm or more. The metallic enclosure's walls are grounded and this arrangement thus forms a Faraday cage. All metal components within the chamber are grounded.

FIG. 31 illustrates an energy diagram, showing a summary of measurement modes for a semiconductor PET/CPD/SPV/SPS, with electrons 3100 represented as before. In the figure:

Photoelectron Threshold=Valence Band
Maximum=$eV_d + e\chi_S + E_g$

CPD(Dark)=Semiconductor Work Function,
$e\phi_S = eV_d + e\chi_S + eV_S + eV_n$

SPV=CPD(Illuminated)−CPD(Dark)=Semiconductor Surface Potential, $eV_S$

SPS=CPD (Illuminated, variable Wavelength), Semiconductor Bandgap, $E_g$
ΔCPD (Oxide Coated Surface-Clean Surface)=$eV_d$
$\phi_S$=Semiconductor Work function
$E_f$=Semiconductor Fermi-level
e=electronic charge
$\chi_S$=the semiconductor electron affinity
$E_g$=the semiconductor band-gap energy
$V_S$=the semiconductor surface potential
$eV_d$=the energy difference across an oxide or other layer representing the atmospheric coating
$eV_n$=the energy difference between the conduction band and the fermi-level
$eV_p$=the energy difference between the valence band and the fermi-level FIG. 32 illustrates an energy diagram, showing a summary of measurement modes for a semiconductor PET/CPD/SPV/SPS, and with electrons 3200 represented as before. In the figure, two different spectrographic methods are outlined—Surface Photoemission Spectroscopy, where UV light is used to liberate electrons from energy levels below the VBM (this technique can be applied to both metals and semiconductors); and Surface Photovoltage Spectroscopy, where external illumination is used to promote electrons to and from surface states within a semiconductor bandgap.

Various improvements and modifications can be made to the above without departing from the scope of the invention.

The invention claimed is:

1. A measurement apparatus comprising:
 a measurement device comprising a probe and being capable of measuring a contact potential difference between the probe and a surface; and
 a light source; wherein the light source is configured to, in use, emit radiation for triggering photoelectric emission from a sample which forms the surface;
 wherein the probe and the surface are exposed to or housed within a gaseous environment; and wherein:
 the probe is selectively operable in a first mode for the performance of a relative work function measurement of the sample and a second mode wherein, for successive photon energy measurements, the probe is in a fixed relation to the surface in a direction normal to the surface for measuring an absolute work function of the same sample derived from detected photoelectric emission, whereby the apparatus advantageously enables measurement of both absolute work function making use of the photoelectric emission and relative work function making use of the contact potential difference employing the same probe and the same sample.

2. The apparatus of claim 1, wherein the gaseous environment comprises air.

3. The apparatus of claim 1 further comprising a housing containing the probe and/or the surface, and the environment within the housing is controlled to provide a gaseous environment having gas or air with a controlled relative humidity or a controlled nitrogen gas.

4. The apparatus of claim 1, wherein the probe comprises a Kelvin probe.

5. The apparatus of claim 1, wherein radiation emitted from the light source is of constant intensity (DC).

6. The apparatus of claim 1, wherein radiation emitted from the light source is modulated (AC).

7. The apparatus of claim 6, comprising an optical chopper for modulating the radiation emitted from the light source.

8. The Apparatus of claim 1, wherein said first and second modes are performed simultaneously or quasi-simultaneously.

9. The apparatus of claim 1, wherein the light source is an ultra-violet broad band source.

10. The apparatus of claim 1, wherein the light source comprises one or more light emitting diodes.

11. The apparatus of claim 10, wherein, multiple LEDs can be individually automatically or selectively controlled in respect of one or more of their intensity, phase and modulation frequency characteristics.

12. The apparatus of claim 1, comprising a second light source for emitting radiation in the visible and/or infrared ranges.

13. The apparatus of claim 12, wherein the light source is arranged to emit a single frequency of light which is used for the performance of a surface photovoltage technique.

14. The apparatus of claim 12, wherein the frequency of light emitted from the light source is varied to perform a surface photovoltage spectroscopy method.

15. The apparatus of claim 12, comprising a chopper that modulates light emitted from the second lightsource.

16. The apparatus of claim 1, comprising a mechanism for scanning the sample with respect to a probe tip to map out the parameters across the surface of the sample.

17. The apparatus of claim 1, wherein said sample comprises any one of: a (bulk) metal, metal alloy, semiconductor, insulator, liquid, polymer, composite, conducting polymer, biological tissue, powder or liquid surface with or without a thin film.

18. The apparatus of claim 1, wherein a tip of the probe has a shape comprising a circle with a section or sections removed.

19. The apparatus of claim 1, being wherein the probe is held at a constant positive voltage and is held in fixed relation to the surface; the energy of photons is scanned, the photoemission current is detected in either DC or AC mode; and a surface density of states (DOS) information is obtained by differentiating the integral current.

20. The apparatus of claim 1, wherein the photon energy is held constant at an energy resulting in photoemission, the probe is held in fixed relation to the surface; the tip potential is scanned through a voltage range; the photoemission current is detected in either DC or AC mode; and a surface density of states (DOS) information is obtained by differentiating the integral current.

21. The method of claim 1, further comprising a wavelength selector through which the radiation emitting from the light source is filtered.

22. The apparatus of claim 1, wherein the light source is an ultra-violet broad band source and is provided with an optical chopper for modulating the radiation emitted from the light source; the apparatus further comprising a second light source for emitting radiation in the visible and/or infrared ranges and provided with a chopper that modulates light emitted from the second light source; and wherein a chopping frequency of the ultra-violet light source can be selected to be different to a chopping frequency of the visible/infrared light source so that measurements using the two different light sources can be conducted in a simultaneous or quasi-simultaneous fashion.

23. A method of analysing a surface comprising the steps of measuring a contact potential difference between a probe and a surface; and emitting radiation for triggering photoelectric emission from a sample which forms the surface; wherein the probe and the surface are exposed to or housed within a gaseous environment, and wherein the probe is selectively operable in a first mode for the performance of a relative work function measurement of the sample and a second mode wherein, for successive photon energy measurements, the probe is in a fixed relation to the surface in a direction normal to the surface for measuring an absolute work function of the same sample derived from detected photoelectric emission, whereby the method advantageously enables measurement of both absolute work function making use of the photoelectric emission and relative work function making use of the contact potential difference employing the same probe and the same sample.

24. The method of claim 23, comprising the further step of filtering the radiation emitting from the light source through a wavelength selector.

25. A computer operating a computer program product encoded with instructions that, when run on the computer, cause the computer to act as a control mechanism for a measurement apparatus, the measurement apparatus comprising:
  a measurement device comprising a probe and being capable of measuring a contact potential difference between the probe and a surface; and
  a light source; wherein the light source is configured to, in use, emit radiation for triggering photoelectric emission from a sample which forms the surface;
  wherein the probe and the surface are exposed to or housed within a gaseous environment; and wherein:
  the probe is selectively operable in a first mode for the performance of a relative work function measurement and a second mode wherein, for successive photon energy measurements, the probe is in a fixed relation to the surface in a direction normal to the surface for measuring an absolute work function of the same sample derived from detected photoelectric emission, whereby the apparatus in cooperation with the computer operating the computer program product advantageously enables measurement of both absolute work function making use of the photoelectric emission and relative work function making use of the contact potential difference employing the same probe and the same sample.

26. The computer of claim 25 wherein the measurement apparatus further comprises a wavelength selector through which the radiation emitting from the light source is filtered.

* * * * *